United States Patent
Demarest et al.

(10) Patent No.: US 11,939,381 B2
(45) Date of Patent: Mar. 26, 2024

(54) BISPECIFIC ANTIBODIES TARGETING IMMUNE CHECKPOINTS

(71) Applicant: Eli Lilly and Company, Indianapolis, IN (US)

(72) Inventors: Stephen J. Demarest, San Diego, CA (US); Yiqing Feng, Carmel, IN (US); Juqun Shen, San Diego, CA (US); Yang Shen, Scarsdale, NY (US); Stephanie Marie Truhlar, Carlsbad, CA (US)

(73) Assignee: Eli Lilly and Company, Indianapolis, IN (US)

( * ) Notice: Subject to any disclaimer, the term of this patent is extended or adjusted under 35 U.S.C. 154(b) by 698 days.

(21) Appl. No.: 17/258,348

(22) PCT Filed: Jul. 12, 2019

(86) PCT No.: PCT/US2019/041517
§ 371 (c)(1),
(2) Date: Jan. 6, 2021

(87) PCT Pub. No.: WO2020/018354
PCT Pub. Date: Jan. 23, 2020

(65) Prior Publication Data
US 2021/0292416 A1  Sep. 23, 2021

Related U.S. Application Data

(60) Provisional application No. 62/799,274, filed on Jan. 31, 2019, provisional application No. 62/700,525, filed on Jul. 19, 2018.

(51) Int. Cl.
*C07K 16/28* (2006.01)
*A61K 39/00* (2006.01)

(52) U.S. Cl.
CPC ...... *C07K 16/2818* (2013.01); *C07K 16/2878* (2013.01); *A61K 2039/505* (2013.01); *C07K 2317/31* (2013.01); *C07K 2317/34* (2013.01); *C07K 2317/75* (2013.01); *C07K 2317/76* (2013.01); *C07K 2317/92* (2013.01)

(58) Field of Classification Search
CPC ............ C07K 16/2818; C07K 16/2878; C07K 2317/31; C07K 2317/34; C07K 2317/75; C07K 2317/76; C07K 2317/92; A61K 2039/505; A61P 35/00
See application file for complete search history.

(56) References Cited

U.S. PATENT DOCUMENTS

| | | | |
|---|---|---|---|
| 2017/0044260 A1* | 2/2017 | Baruah | A61P 43/00 |
| 2018/0319880 A1* | 11/2018 | Benschop | A61K 39/395 |
| 2019/0010232 A1* | 1/2019 | Kalos | C07K 16/2818 |
| 2020/0377607 A1* | 12/2020 | Frye | A61P 35/00 |

FOREIGN PATENT DOCUMENTS

| | | | |
|---|---|---|---|
| WO | 2015/119923 A1 | 8/2015 | |
| WO | 2016/134358 A1 | 8/2016 | |
| WO | 2017/024465 A1 | 2/2017 | |
| WO | 2017/025016 A1 | 2/2017 | |
| WO | 2017/133540 A1 | 8/2017 | |
| WO | 2018/045110 A1 | 3/2018 | |
| WO | 2019/027754 A1 | 2/2019 | |
| WO | WO-2019027754 A1 * | 2/2019 | A61K 39/3955 |

OTHER PUBLICATIONS

Anthony W. Tolcher, et al., "Phase Ib Study of Utomilumab (PF-05082566), a 4-1BB/CD137 Agonist, in Combination with Pembrolizumab (MK-3475) in Patients with Advanced Solid Tumors," Clinical Cancer Research, vol. 23, No. 18, pp. 5349-5357 (Sep. 15, 2017).
Elisabeth Perez-Ruiz, et al., "Anti-CD137 and PD-1/PD-L1 Antibodies En Route toward Clinical Synergy," Clinical Cancer Research, vol. 23, No. 18, pp. 5326-5328 (Aug. 8, 2017).
Shindo Y, et al., "Combination immunotherapy with 4-1BB activation and PD-1 blockade enhances antitumor efficacy in a mouse model of subcutaneous tumor," Anticancer Research—International Journal of Cancer Research and Treatment, International Institute of Anticancer Research, GR, vol. 35, No. 1, pp. 129-136 (2015).
Eva Dahlen, et al., "Bispecific antibodies in cancer immunotherapy," Therapeutic Advances in Vaccines and Immunotherapy, vol. 6, No. 1, pp. 3-17 (Feb. 28, 2018).
Ulrich Brinkmann, et al., "The making of bispecific antibodies," MABS, vol. 9, No. 2, pp. 182-212 (Jan. 10, 2017).
International Search Report for International Application No. PCT/US2019/041517, European Patent Office, Munich, Germany, dated Oct. 24, 2019.
Written Opinion for International Application No. PCT/US2019/041517, European Patent Office, Munich, Germany, dated Oct. 24, 2019.

* cited by examiner

*Primary Examiner* — Julie Wu
*Assistant Examiner* — John L Van Druff
(74) *Attorney, Agent, or Firm* — Robert Brian Johnson

(57) ABSTRACT

The present invention relates to bispecific antibodies that antagonize human PD-1 and agonize human CD137, and may be useful for treating solid and hematological tumors alone and in combination with chemotherapy and ionizing radiation.

20 Claims, No Drawings
Specification includes a Sequence Listing.

SEQUENCE LISTING

<160> NUMBER OF SEQ ID NOS: 37

<210> SEQ ID NO 1
<211> LENGTH: 13
<212> TYPE: PRT
<213> ORGANISM: Artificial Sequence
<220> FEATURE:
<223> OTHER INFORMATION: Synthetic Construct

<400> SEQUENCE: 1

Lys Ala Ser Gly Gly Thr Phe Ser Ser Tyr Ala Ile Ser
1               5                   10

<210> SEQ ID NO 2
<211> LENGTH: 17
<212> TYPE: PRT
<213> ORGANISM: Artificial Sequence
<220> FEATURE:
<223> OTHER INFORMATION: Synthetic Construct

<400> SEQUENCE: 2

Gly Ile Ile Pro Ile Phe Gly Thr Ala Asn Tyr Ala Gln Lys Phe Gln
1               5                   10                  15

Gly

<210> SEQ ID NO 3
<211> LENGTH: 15
<212> TYPE: PRT
<213> ORGANISM: Artificial Sequence
<220> FEATURE:
<223> OTHER INFORMATION: Synthetic Construct

<400> SEQUENCE: 3

Ala Arg Asp Leu Ala Thr Thr Ala Pro Ala Thr Tyr Phe Asp Leu
1               5                   10                  15

<210> SEQ ID NO 4
<211> LENGTH: 122
<212> TYPE: PRT
<213> ORGANISM: Artificial Sequence
<220> FEATURE:
<223> OTHER INFORMATION: Synthetic Construct

<400> SEQUENCE: 4

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

```
Ala Ile Ser Trp Val Arg Tyr Ala Pro Gly Gln Gly Leu Glu Trp Met
            35                  40                  45

Gly Gly Ile Ile Pro Ile Phe Gly Thr Ala Asn Tyr Ala Gln Lys Phe
 50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Asp Leu Ala Thr Thr Ala Pro Ala Thr Tyr Phe Asp Leu Trp
                100                 105                 110

Gly Arg Gly Thr Leu Val Thr Val Ser Ser
                115                 120
```

<210> SEQ ID NO 5
<211> LENGTH: 452
<212> TYPE: PRT
<213> ORGANISM: Artificial Sequence
<220> FEATURE:
<223> OTHER INFORMATION: Synthetic Construct

<400> SEQUENCE: 5

```
Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
                20                  25                  30

Ala Ile Ser Trp Val Arg Tyr Ala Pro Gly Gln Gly Leu Glu Trp Met
            35                  40                  45

Gly Gly Ile Ile Pro Ile Phe Gly Thr Ala Asn Tyr Ala Gln Lys Phe
 50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Asp Leu Ala Thr Thr Ala Pro Ala Thr Tyr Phe Asp Leu Trp
                100                 105                 110

Gly Arg Gly Thr Leu Val Thr Val Ser Ser Ala Ser Thr Lys Gly Pro
                115                 120                 125

Ser Val Phe Pro Leu Ala Pro Cys Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Pro Ser Ser Ser Leu Gly Thr Gln Thr Tyr Ile Cys Asn Val Asn
                195                 200                 205

His Lys Pro Ser Asn Thr Lys Val Asp Lys Arg Val Glu Pro Asp Ser
    210                 215                 220

Gly Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
                260                 265                 270
```

His Glu Asp Pro Glu Val Lys Phe Asn Trp Tyr Val Asp Gly Val Glu
         275                 280                 285

Val His Asn Ala Lys Thr Lys Pro Arg Glu Glu Gln Tyr Gln Ser Thr
     290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
             325                 330                 335

Ile Glu Lys Thr Ile Ser Lys Ala Lys Gly Gln Pro Arg Glu Pro Gln
         340                 345                 350

Val Tyr Thr Leu Pro Pro Ser Arg Gly Asp Met Thr Lys Asn Gln Val
     355                 360                 365

Gln Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Ala Ser Lys Leu Thr
             405                 410                 415

Val Asp Lys Ser Arg Trp Gln Gln Gly Asn Val Phe Ser Cys Ser Val
         420                 425                 430

Met His Glu Ala Leu His Asn His Tyr Thr Gln Lys Ser Leu Ser Leu
     435                 440                 445

Ser Pro Gly Lys
    450

```
<210> SEQ ID NO 6
<211> LENGTH: 1356
<212> TYPE: DNA
<213> ORGANISM: Artificial Sequence
<220> FEATURE:
<223> OTHER INFORMATION: Synthetic Construct

<400> SEQUENCE: 6
caggttcagt tggtgcaatc aggcgcagag gtaaaaaaac cagggtccag cgtgaaagtc    60
tcatgtaagg cctccggcgg aacattctcc tcctacgcta tttcttgggt gagatacgcc   120
cctgggcagg gacttgagtg gatgggaggc attattccca tattcggcac agccaattac   180
gcgcaaaaat tccaggggag ggttactata acagcagatg agagtacatc aactgcgtac   240
atggaactga gctccctgag gagcgaagac accgctgttt actactgcgc tagagatctt   300
gcgacgaccg cacctgcgac gtactttgat ctctggggta gaggaaccct cgtaacagtg   360
tcttccgcta gcaccaaggg cccatcggtc ttccccctgg caccctgctc aagagcacc    420 tctgggggca gcggccct gggctgcctg gtcaaggact acttcccga accggtgacg     480 gtgtcgtgga actcaggcgc cctgaccagc ggcgtgcaca ccttcccggc tgtcctacag    540
tcctcaggac tctactccct cagcagcgtg gtgaccgtgc cctccagcag cttgggcacc    600
cagacctaca tctgcaacgt gaatcacaag cccagcaaca ccaaggtgga caagagagtt    660
gagcccgatt ctggtgacaa aactcacaca tgcccaccgt gcccagcacc tgaagccgcc    720
gggggaccgt cagtcttcct cttccccca aaacccaagg acaccctcat gatctcccgg    780
acccctgagg tcacatgcgt ggtggtggac gtgagccacg aagaccctga ggtcaagttc    840
aactggtatg tggacggcgt ggaggtgcat aatgccaaga caaagccgcg ggaggagcag    900
taccagagca cgtaccgtgt ggtcagcgtc ctcaccgtcc tgcaccaaga ctggctgaat    960
```

```
ggcaaggagt acaagtgcaa ggtctccaac aaagccctcc cagcccccat cgagaaaacc    1020
atctccaaag ccaaagggca gccccgagaa ccacaggtgt acaccctgcc cccatcccgg    1080
ggggacatga ccaagaacca gtccagctg acctgcctgg tcaaaggctt ctatcccagc    1140
gacatcgccg tggagtggga gagcaatggg cagccggaga caactacaa gaccacgcct    1200 cccgtgctgg actccgacgg ctccttcttc ctcgcttcca agctcaccgt ggacaagagc    1260
aggtggcagc aggggaacgt cttctcatgc tccgtgatgc atgaggctct gcacaaccac    1320
tacacgcaga agagcctctc cctgtctccg ggcaaa                              1356
```

<210> SEQ ID NO 7
<211> LENGTH: 11
<212> TYPE: PRT
<213> ORGANISM: Artificial Sequence
<220> FEATURE:
<223> OTHER INFORMATION: Synthetic Construct

<400> SEQUENCE: 7

```
Gln Ala Ser Gln Asp Ile Gly Asn Ser Leu Gly
1               5                   10
```

<210> SEQ ID NO 8
<211> LENGTH: 8
<212> TYPE: PRT
<213> ORGANISM: Artificial Sequence
<220> FEATURE:
<223> OTHER INFORMATION: Synthetic Construct

<400> SEQUENCE: 8

```
Phe Asp Ala Ser Asp Leu Glu Thr
1               5
```

<210> SEQ ID NO 9
<211> LENGTH: 9
<212> TYPE: PRT
<213> ORGANISM: Artificial Sequence
<220> FEATURE:
<223> OTHER INFORMATION: Synthetic Construct

<400> SEQUENCE: 9

```
Gln Gln Gly Asn Ser Phe Pro Leu Thr
1               5
```

<210> SEQ ID NO 10
<211> LENGTH: 107
<212> TYPE: PRT
<213> ORGANISM: Artificial Sequence
<220> FEATURE:
<223> OTHER INFORMATION: Synthetic Construct

<400> SEQUENCE: 10

```
Asp Ile Arg Met Thr Gln Ser Pro Ser Leu Ser Ala Ser Val Gly
1               5                   10                  15

Asp Arg Val Thr Ile Thr Cys Gln Ala Ser Gln Asp Ile Gly Asn Ser
                20                  25                  30

Leu Gly Trp Tyr Gln Arg Lys Pro Gly Asp Ala Pro Lys Leu Val Ile
            35                  40                  45

Phe Asp Ala Ser Asp Leu Glu Thr Gly Val Pro Ser Arg Phe Ser Gly
        50                  55                  60

Ser Gly Ser Gly Thr Asp Phe Ser Leu Thr Ile Ser Ser Leu Gln Pro
65                  70                  75                  80

Glu Asp Phe Ala Thr Tyr Tyr Cys Gln Gln Gly Asn Ser Phe Pro Leu
```

85                  90                  95

Thr Phe Gly Gln Gly Thr Arg Leu Glu Ile Lys
            100                 105

<210> SEQ ID NO 11
<211> LENGTH: 214
<212> TYPE: PRT
<213> ORGANISM: Artificial Sequence
<220> FEATURE:
<223> OTHER INFORMATION: Synthetic Construct

<400> SEQUENCE: 11

Asp Ile Arg Met Thr Gln Ser Pro Ser Leu Ser Ala Ser Val Gly
1               5                   10                  15

Asp Arg Val Thr Ile Thr Cys Gln Ala Ser Gln Asp Ile Gly Asn Ser
            20                  25                  30

Leu Gly Trp Tyr Gln Arg Lys Pro Gly Asp Ala Pro Lys Leu Val Ile
        35                  40                  45

Phe Asp Ala Ser Asp Leu Glu Thr Gly Val Pro Ser Arg Phe Ser Gly
    50                  55                  60

Ser Gly Ser Gly Thr Asp Phe Ser Leu Thr Ile Ser Ser Leu Gln Pro
65                  70                  75                  80

Glu Asp Phe Ala Thr Tyr Tyr Cys Gln Gln Gly Asn Ser Phe Pro Leu
                85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Lys Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 12
<211> LENGTH: 642
<212> TYPE: DNA
<213> ORGANISM: Artificial Sequence
<220> FEATURE:
<223> OTHER INFORMATION: Synthetic Construct

<400> SEQUENCE: 12
gacattagaa tgacacagtc acctccaagt ctgtcagcca gtgttggcga ccgggtgact      60
atcacctgcc aggcttccca agacattggt aatagtttgg gttggtacca gcgcaaacca     120
ggcgatgctc cgaaactggt tattttgac gccagtgatt tggagacagg tgtgccttct     180
cggtttagcg gttctgggtc aggaactgat ttttcactga caatatcttc actgcagccg     240
gaagacttcg ccacctatta ttgccagcag gggaactcct tcccactcac cttcggtcaa     300
gggacccggc ttgagattaa gcggacggta gctgccccct ctgtgttcat tttcccccca     360

```
agcaaggagc agctgaagag cggcacggcc agcgtggtat gtctgctgaa taactttac      420 cctcgggagg ccaaagtgca gtggaaggtc gataatgctc ttcaatccgg gaactcacag     480
gaatctgtca ccgaacaaga cagcaaggat agcacgtaca gcctgtctag cactctgacc     540
ctttccaaag cagactacga aaaacataaa gtctacgcgt gcgaagtgac ccaccagggg    600
ctcagctcac cggtgacgaa atccttcaac cgcggcgaat gc                       642
```

<210> SEQ ID NO 13
<211> LENGTH: 13
<212> TYPE: PRT
<213> ORGANISM: Artificial Sequence
<220> FEATURE:
<223> OTHER INFORMATION: Synthetic Construct

<400> SEQUENCE: 13

Lys Ala Ser Gly Gly Thr Phe Ser Ser Tyr Ala Ile Ser
1               5                   10

<210> SEQ ID NO 14
<211> LENGTH: 17
<212> TYPE: PRT
<213> ORGANISM: Artificial Sequence
<220> FEATURE:
<223> OTHER INFORMATION: Synthetic Construct

<400> SEQUENCE: 14

Leu Ile Ile Pro Ser Phe Asp Thr Ala Gly Tyr Ala Gln Glu Phe Gln
1               5                   10                  15

Gly

<210> SEQ ID NO 15
<211> LENGTH: 13
<212> TYPE: PRT
<213> ORGANISM: Artificial Sequence
<220> FEATURE:
<223> OTHER INFORMATION: Synthetic Construct

<400> SEQUENCE: 15

Ala Arg Ala Glu His Ser Ser Thr Gly Thr Phe Asp Tyr
1               5                   10

<210> SEQ ID NO 16
<211> LENGTH: 120
<212> TYPE: PRT
<213> ORGANISM: Artificial Sequence
<220> FEATURE:
<223> OTHER INFORMATION: Synthetic Construct

<400> SEQUENCE: 16

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Lys Ala Pro Gly Gln Gly Leu Glu Trp Met
            35                  40                  45

Gly Leu Ile Ile Pro Ser Phe Asp Thr Ala Gly Tyr Ala Gln Glu Phe
        50                  55                  60

Gln Gly Arg Val Ala Ile Thr Val Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

```
Ala Arg Ala Glu His Ser Ser Thr Gly Thr Phe Asp Tyr Trp Gly Gln
            100                 105                 110

Gly Thr Leu Val Thr Val Ser Ser
        115                 120

<210> SEQ ID NO 17
<211> LENGTH: 450
<212> TYPE: PRT
<213> ORGANISM: Artificial Sequence
<220> FEATURE:
<223> OTHER INFORMATION: Synthetic Construct

<400> SEQUENCE: 17

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Lys Ala Pro Gly Gln Gly Leu Glu Trp Met
        35                  40                  45

Gly Leu Ile Ile Pro Ser Phe Asp Thr Ala Gly Tyr Ala Gln Glu Phe
    50                  55                  60

Gln Gly Arg Val Ala Ile Thr Val Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Glu His Ser Ser Thr Gly Thr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Gln Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335
```

| | | | | | | | | | | | |
|---|---|---|---|---|---|---|---|---|---|---|---|
|Lys|Thr|Ile|Ser|Lys|Ala|Lys|Gly|Gln|Pro|Arg|Glu|Pro|Gln|Val|Ser|
| | |340| | | | |345| | | | |350| | |

Lys Thr Ile Ser Lys Ala Lys Gly Gln Pro Arg Glu Pro Gln Val Ser
              340                 345                 350

Thr Leu Pro Pro Ser Arg Glu Glu Met Thr Lys Asn Gln Val Ser Leu
            355                 360                 365

Met Cys Leu Val Tyr Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Val Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 18
<211> LENGTH: 1350
<212> TYPE: DNA
<213> ORGANISM: Artificial Sequence
<220> FEATURE:
<223> OTHER INFORMATION: Synthetic Construct

<400> SEQUENCE: 18

```
caagtgcaac tggtgcaatc aggggctgag gtgaagaagc ctggaagtag cgttaaagtc      60
agttgcaaag cgtccggtgg gacatttagc agctatgcca tcagctgggt tcggaaggca     120
cccggccagg gactggagtg gatgggactc ataatcccga gctttgacac tgctggttac     180
gcacaggagt ttcaagggag ggtggcgatc acagtggacg aatcaaccag caccgcgtat     240
atggagctgt catctctgag gtcagaagac accgctgttt actattgtgc ccgcgctgag     300
cattcttcca ccgggacctt cgattactgg ggacaaggaa ccctggtcac agtatcatca     360
gctagcacca agggcccatc ggtcttcccc ctggcaccct cctccaagag cacctctggg     420
ggcacagcgg ccctgggctg cctggtcaag gactacttcc ccgaaccggt gacggtgtcg     480
tggaactcag gcgccctgac cagcggcgtg gccaccggcc cggctgtcct acagtcctca     540
ggactctact ccctcagcag cgtggtgacc gtgccctcca gcagcttggg cacccagacc     600
tacatctgca acgtgaatca caagcccagc aacaccaagg tggacaagag agttgagccc     660
aaatcttgtg acaaaactca cacatgccca ccgtgcccag cacctgaagc cgccggggga     720
ccgtcagtct tcctcttccc cccaaaaccc aaggacaccc tcatgatctc ccggacccct     780
gaggtcacat gcgtggtggt ggacgtgagc cacgaagacc ctgaggtcaa gttcaactgg     840
tatgtggacg gcgtggaggt gcataatgcc aagacaaagc cgcgggagga gcagtaccag     900
agcacgtacc gtgtggtcag cgtcctcacc gtcctgcacc aagactggct gaatggcaag     960
gagtacaagt gcaaggtctc caacaaagcc ctcccagccc ccatcgagaa aaccatctcc    1020
aaagccaaag gcagccccg agaaccacag gtgtccaccc tgcccccatc ccgggaggag    1080
atgaccaaga accaagtcag cctgatgtgc ctggtctatg gcttctatcc cagcgacatc    1140
gccgtggagt gggagagcaa tgggcagccg gagaacaact acaagaccac gcctcccgtg    1200
ctggactccg acggctcctt cttcctctat tccgtgctca ccgtggacaa gagcaggtgg    1260
cagcagggga acgtcttctc atgctccgtg atgcatgagg ctctgcacaa ccactacacg    1320
cagaagagcc tctccctgtc tccgggcaaa                                    1350
```

<210> SEQ ID NO 19
<211> LENGTH: 11
<212> TYPE: PRT
<213> ORGANISM: Artificial Sequence
<220> FEATURE:
<223> OTHER INFORMATION: Synthetic Construct

<400> SEQUENCE: 19

Arg Ala Ser Gln Gly Ile Ser Ser Trp Leu Ala
1               5                   10

<210> SEQ ID NO 20
<211> LENGTH: 8
<212> TYPE: PRT
<213> ORGANISM: Artificial Sequence
<220> FEATURE:
<223> OTHER INFORMATION: Synthetic Construct

<400> SEQUENCE: 20

Ser Ala Ala Ser Ser Leu Gln Ser
1               5

<210> SEQ ID NO 21
<211> LENGTH: 9
<212> TYPE: PRT
<213> ORGANISM: Artificial Sequence
<220> FEATURE:
<223> OTHER INFORMATION: Synthetic Construct

<400> SEQUENCE: 21

Gln Gln Ala Asn His Leu Pro Phe Thr
1               5

<210> SEQ ID NO 22
<211> LENGTH: 107
<212> TYPE: PRT
<213> ORGANISM: Artificial Sequence
<220> FEATURE:
<223> OTHER INFORMATION: Synthetic Construct

<400> SEQUENCE: 22

Arg Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Asp Lys Pro Gly Lys Ala Pro Lys Leu Leu Ile
        35                  40                  45

Ser Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn His Leu Pro Phe
                85                  90                  95

Thr Phe Gly Gly Gly Thr Lys Val Glu Ile Lys
            100                 105

<210> SEQ ID NO 23
<211> LENGTH: 212
<212> TYPE: PRT
<213> ORGANISM: Artificial Sequence
<220> FEATURE:
<223> OTHER INFORMATION: Synthetic Construct

<400> SEQUENCE: 23

```
Arg Ile Gln Met Thr Gln Ser Pro Ser Ser Val Ser Ala Ser Val Gly
1               5                   10                  15
Asp Arg Val Thr Ile Thr Cys Arg Ala Ser Gln Gly Ile Ser Ser Trp
            20                  25                  30
Leu Ala Trp Tyr Gln Asp Lys Pro Gly Lys Ala Pro Lys Leu Leu Ile
        35                  40                  45
Ser Ala Ala Ser Ser Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Ala Asn His Leu Pro Phe
                85                  90                  95
Thr Phe Gly Gly Gly Thr Lys Val Glu Ile Lys Gly Gln Pro Lys Ala
            100                 105                 110
Ala Pro Ser Val Thr Leu Phe Pro Pro Ser Ser Glu Glu Leu Gln Ala
        115                 120                 125
Asn Lys Ala Thr Leu Val Cys Tyr Ile Ser Asp Phe Tyr Pro Gly Ala
    130                 135                 140
Val Thr Val Ala Trp Lys Ala Asp Ser Ser Pro Val Lys Ala Gly Val
145                 150                 155                 160
Glu Thr Thr Thr Pro Ser Lys Gln Ser Asn Asn Lys Tyr Ala Ala Trp
                165                 170                 175
Ser Tyr Leu Ser Leu Thr Pro Glu Gln Trp Lys Ser His Arg Ser Tyr
            180                 185                 190
Ser Cys Gln Val Thr His Glu Gly Ser Thr Val Glu Lys Thr Val Ala
        195                 200                 205
Pro Thr Glu Cys
    210
```

<210> SEQ ID NO 24
<211> LENGTH: 636
<212> TYPE: DNA
<213> ORGANISM: Artificial Sequence
<220> FEATURE:
<223> OTHER INFORMATION: Synthetic Construct

<400> SEQUENCE: 24

```
cgcatccaga tgacacagtc accttcaagc gtctccgcct ccgtgggaga cagggttact    60
attacatgta gggccagcca ggggatctct tcatggctgg cgtggtacca agacaagcca   120
ggcaaagccc ccaagctcct tatctccgct gcctcctctc tgcagtccgg agttccctcc   180
cgcttcagcg gtagcgggtc aggcactgac ttcaccctta caatctcttc tctgcaacct   240
gaggacttcg ccacatatta ttgccagcag gcaaaccatt tgccatttac ttttggcgga   300
ggtactaagg ttgagattaa aggccagcct aaagctgccc ctagcgttac ccttttccca   360
ccgagctccg aggagctgca ggccaataaa gcaaccttgg tctgctacat atcagatttt   420
taccctggcg ccgtgaccgt agcatggaaa gctgattcat ccctgtgaa ggccggtgtt    480
gaaactacaa cccctttccaa acaatctaac aataaatacg cggcatggtc ctacctgtcc   540
ttgacacccg agcagtggaa atctcacaga tcttacagct gccaggtcac ccacgagggg   600
agcactgtgg agaagaccgt cgcgcccact gagtgc                              636
```

<210> SEQ ID NO 25
<211> LENGTH: 288

```
<212> TYPE: PRT
<213> ORGANISM: Homo sapiens

<400> SEQUENCE: 25

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285

<210> SEQ ID NO 26
<211> LENGTH: 255
<212> TYPE: PRT
<213> ORGANISM: Homo sapiens

<400> SEQUENCE: 26

Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
            20                  25                  30

Ala Gly Thr Phe Cys Asp Asn Asn Arg Asn Gln Ile Cys Ser Pro Cys
        35                  40                  45

Pro Pro Asn Ser Phe Ser Ser Ala Gly Gly Gln Arg Thr Cys Asp Ile
    50                  55                  60
```

```
Cys Arg Gln Cys Lys Gly Val Phe Arg Thr Arg Lys Glu Cys Ser Ser
 65                  70                  75                  80

Thr Ser Asn Ala Glu Cys Asp Cys Thr Pro Gly Phe His Cys Leu Gly
                 85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
        115                 120                 125

Lys Arg Gly Ile Cys Arg Pro Trp Thr Asn Cys Ser Leu Asp Gly Lys
130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
        195                 200                 205

Arg Phe Ser Val Val Lys Arg Gly Arg Lys Lys Leu Leu Tyr Ile Phe
210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu
                245                 250                 255

<210> SEQ ID NO 27
<211> LENGTH: 330
<212> TYPE: PRT
<213> ORGANISM: Homo sapiens

<400> SEQUENCE: 27

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190
```

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 28
<211> LENGTH: 105
<212> TYPE: PRT
<213> ORGANISM: Homo sapiens

<400> SEQUENCE: 28

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys
            100                 105

<210> SEQ ID NO 29
<211> LENGTH: 107
<212> TYPE: PRT
<213> ORGANISM: Homo sapiens

<400> SEQUENCE: 29

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
              85                  90                  95

Pro Val Thr Lys Ser Phe Asn Arg Gly Glu Cys
            100                 105

<210> SEQ ID NO 30
<211> LENGTH: 330
<212> TYPE: PRT
<213> ORGANISM: Artificial Sequence
<220> FEATURE:
<223> OTHER INFORMATION: Synthetic Construct

<400> SEQUENCE: 30

Ala Ser Thr Lys Gly Pro Ser Val Phe Pro Leu Ala Pro Cys Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Asp Ser Gly Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Gln Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Gly Asp
225                 230                 235                 240

Met Thr Lys Asn Gln Val Gln Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Ala Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

```
<210> SEQ ID NO 31
<211> LENGTH: 107
<212> TYPE: PRT
<213> ORGANISM: Artificial Sequence
<220> FEATURE:
<223> OTHER INFORMATION: Synthetic Construct

<400> SEQUENCE: 31

Arg Thr Val Ala Ala Pro Ser Val Phe Ile Phe Pro Pro Ser Lys Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 32
<211> LENGTH: 330
<212> TYPE: PRT
<213> ORGANISM: Artificial Sequence
<220> FEATURE:
<223> OTHER INFORMATION: Synthetic Construct

<400> SEQUENCE: 32

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val Ala Thr Gly Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Gln Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
```

```
            195                 200                 205
Lys Ala Leu Pro Ala Pro Ile Glu Lys Thr Ile Ser Lys Ala Lys Gly
    210                 215                 220

Gln Pro Arg Glu Pro Gln Val Ser Thr Leu Pro Pro Ser Arg Glu Glu
225                 230                 235                 240

Met Thr Lys Asn Gln Val Ser Leu Met Cys Leu Val Tyr Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Val Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 33
<211> LENGTH: 105
<212> TYPE: PRT
<213> ORGANISM: Artificial Sequence
<220> FEATURE:
<223> OTHER INFORMATION: Synthetic Construct

<400> SEQUENCE: 33

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Tyr Ile Ser Asp
                20                  25                  30

Phe Tyr Pro Gly Ala Val Thr Val Ala Trp Lys Ala Asp Ser Ser Pro
            35                  40                  45

Val Lys Ala Gly Val Glu Thr Thr Thr Pro Ser Lys Gln Ser Asn Asn
    50                  55                  60

Lys Tyr Ala Ala Trp Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys
                100                 105

<210> SEQ ID NO 34
<211> LENGTH: 122
<212> TYPE: PRT
<213> ORGANISM: Artificial Sequence
<220> FEATURE:
<223> OTHER INFORMATION: Synthetic Construct

<400> SEQUENCE: 34

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
    50                  55                  60
```

```
Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asp Leu Met Thr Thr Ala Pro Gly Thr Tyr Phe Asp Leu Trp
            100                 105                 110

Gly Arg Gly Thr Leu Val Thr Val Ser Ser
            115                 120

<210> SEQ ID NO 35
<211> LENGTH: 107
<212> TYPE: PRT
<213> ORGANISM: Artificial Sequence
<220> FEATURE:
<223> OTHER INFORMATION: Synthetic Construct

<400> SEQUENCE: 35

Ala Ile Arg Met Thr Gln Ser Pro Pro Ser Leu Ser Ala Ser Val Gly
 1               5                  10                  15

Asp Arg Val Thr Ile Thr Cys Gln Ala Ser Gln Asp Ile Gly Asn Ser
             20                  25                  30

Leu Gly Trp Tyr Gln Gln Lys Pro Gly Lys Ala Pro Lys Leu Val Ile
         35                  40                  45

Phe Asp Ala Ser Asp Leu Glu Thr Gly Val Pro Ser Arg Phe Ser Gly
 50                  55                  60

Ser Gly Ser Gly Thr Asp Phe Ser Leu Thr Ile Ser Ser Leu Gln Pro
 65                  70                  75                  80

Glu Asp Phe Ala Thr Tyr Tyr Cys Gln Gln Gly Asn Ser Phe Pro Leu
                 85                  90                  95

Thr Phe Gly Gln Gly Thr Arg Leu Glu Ile Lys
            100                 105

<210> SEQ ID NO 36
<211> LENGTH: 120
<212> TYPE: PRT
<213> ORGANISM: Artificial Sequence
<220> FEATURE:
<223> OTHER INFORMATION: Synthetic Construct

<400> SEQUENCE: 36

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
             20                  25                  30

Ala Ile Ser Trp Val Arg Gln Ala Pro Gly Gln Gly Leu Glu Trp Met
         35                  40                  45

Gly Leu Ile Ile Pro Met Phe Asp Thr Ala Gly Tyr Ala Gln Lys Phe
 50                  55                  60

Gln Gly Arg Val Ala Ile Thr Val Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ala Glu His Ser Ser Gly Thr Phe Asp Tyr Trp Gly Gln
            100                 105                 110

Gly Thr Leu Val Thr Val Ser Ser
            115                 120

<210> SEQ ID NO 37
```

```
<211> LENGTH: 107
<212> TYPE: PRT
<213> ORGANISM: Artificial Sequence
<220> FEATURE:
<223> OTHER INFORMATION: Synthetic Construct

<400> SEQUENCE: 37

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Ser Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn His Leu Pro Phe
                85                  90                  95

Thr Phe Gly Gly Gly Thr Lys Val Glu Ile Lys
            100                 105
```

BISPECIFIC ANTIBODIES TARGETING IMMUNE CHECKPOINTS

The present invention is in the field of medicine. Particularly, the present invention relates to novel bispecific antibodies that antagonize human programmed celldeath 1 (PD-1) and agonize human CD137, compositions comprising such bispecific antibodies, and methods of using such bispecific antibodies for the treatment of solid and hematological tumors, alone or in combination with chemotherapy and other cancer therapeutics.

Immune checkpoints are a group of membrane proteins expressed on immune cells (e.g., T cells & dendritic cells), including multiple co-inhibitory and co-stimulatory receptors, that play an important role in the regulation of the adaptive immune response. Well studied checkpoint include PD-1 and CD137. The interaction between PD-1 and its ligands, programmed cell death ligand 1 (PD-L1) and programmed cell death ligand 2 (PD-L2), provides an inhibitory signal that has been shown to play a key role in tumor immune escape and the immunosuppression that occurs in the tumor microenvironment. While the blockade of PD-1 inhibitory signaling with anti-PD-1 antibodies and/or anti-PD-L1 antibodies is clinically validated and has led to significant clinical advances for the treatment of certain cancers, there are many patients who either do not respond, relapse, acquire resistance to the PD-1 or PD-L1 antibody treatment(s), or otherwise are intolerant to treatment. CD137, also known as 4-1BB, plays a role in the activation of T cell driven immune responses such as by promoting T cell proliferation and effector functions, boosting immunological memory, and inhibiting activation-induced cell death. Agonistic antibodies targeting CD137 have shown promise in murine tumor models as a monotherapy and as a combination therapy, however, agonistic antibodies targeting human CD137 have not yet demonstrated sufficient responses either as a monotherapy or as a combination therapy in human cancer patients due to toxicity and/or lack of efficacy. Indeed, no agonistic antibody targeting human CD137 has been approved for therapeutic use in humans. Thus, there exists a need for additional treatments that target immune checkpoint pathways.

Combinations of antibodies that agonize CD137 and antagonize PD-1, for example, the combination of urelumab (i.e, an anti-CD137 agonist monoclonal antibody) and nivolumab (i.e., an anti-PD-1 antagonist monoclonal antibody), have been studied in clinical trials for the treatment of solid tumors (Tolcher at al., Clin Cancer Res 23(18) 2017). However, higher potentially efficacious doses of urelumab have been associated with transaminitis and other adverse events. Targetting the CD137 agonistic antibody specifically to those cells that express PD-1 may limit the adverse events associated with the systemic administration of an agonistic CD137 antibody. As such, there exists a need for the bispecific antibodies of the present invention that are designed to provide an immune boost by preferentially binding cells that express PD-1, potentially limiting the effects of CD137 agonism to those cells that also express PD-1.

WO2018/045110 discloses several bispecific antibodies (Fab-scFv-Fc format) that bind to a co-inhibitory receptor and a co-stimulatory receptor to activate T cells for treating cancer, including [ICOS×PD-1] and [CD137×PD-1]. It appears that the CD137 Fab disclosed in WO2018/045110 was derived from BMS20H4.9, which may be associated with the development of severe transaminitis (Segal et al., *Clinical Cancer Research* (2016) 1-8). In contrast to the bispecific antibodies disclosed in WO2018/045110, IgG-like bispecific antibodies have many of the favorable properties associated with natural IgG antibodies, such as high stability, long serum half-lives, and low immunogenicity (Ha et al., *Frontiers in Immunology* (2016) Article 394). Because of the known toxicities associated with BMS20H4.9 and because of the non-desirable structural format of the bispecifics described in WO2018/045110, there exists a need for additional bispecific antibodies that are IgG-like bispecific antibodies that antagonize human PD-1 and agonize human CD137 and promote a robust anti-cancer immune response and display acceptable toxicity profiles.

The bispecific antibodies of the present invention are designed to favor heterodimeric pairing of the two distinct heavy chains and disfavor formation of homodimers. Preferably, the bispecific antibodies described herein contain an Fc portion that is derived from human IgG1. IgG1 is known to bind to the proteins of the Fc-gamma receptor (FcγR) family as well as C1q. IgG1 binding to an FcγR or C1q induces antibody-dependent cellular cytotoxicity (ADCC) and complement-dependent cytotoxicity (CDC), respectively. Therefore, preferably, the antibodies described herein are a human IgG1 engineered to reduce the binding of the antibody to an FcγR as well as C1q. Preferably, amino acid substitutions of positions L234A and L235A in EU numbering are introduced into the CH2 region to reduce the binding of the antibody to an FcγR as well as C1q. Optionally, amino acid substitution of position N297Q in EU numbering is introduced to further reduce the ADCC and CDC activities of the antibody.

Furthermore, the selective mutagenesis that was employed to generate the antibodies described herein (hereafter referred to as "Antibody A") is summarized in Tables 1-7. Additionally, Tables 1-4 show the selective mutagenesis of residues in the variable regions of Antibody A (Anti-CD137 Arm-7A5*/Anti-PD-1 Arm-11444*) as compared to the parental antibodies 7A5 and 11444. Tables 5-7 summarize the selective mutagenesis that was conducted within the constant regions of Antibody A as compared to wild-type human IgG1 and the wild-type (wt) human lambda and kappa. The selective mutagenesis of residues in the two arms of Antibody A, and the parental monoclonal antibodies, anti-CD137 (7A5) and anti-PD-1 (11444), is further summarized in Table 8.

TABLE 1

HCVRs

7A5* QVQLVQSGAEVKKPGSSVKVSCKASGGTFSSYAISWVRYAPGQGLEWMGGIIPIFGTANY
7A5  QVQLVQSGAEVKKPGSSVKVSCKASGGTFSSYAISWVRQAPGQGLEWMGGIIPIFGTANY
     ************************************** ******************

7A5* AQKFQGRVTITADESTSTAYMELSSLRSEDTAVYYCARDLATTAPATYFDLWGRGTLVTV
7A5  AQKFQGRVTITADESTSTAYMELSSLRSEDTAVYYCARDLMTTAPGTYFDLWGRGTLVTV
     ************************************* .************

TABLE 1-continued

HCVRs

```
7A5*  SS (SEQ ID NO: 4)
7A5   SS (SEQ ID NO: 34)
      **
```

TABLE 2

LCVRs

```
7A5*  DIRMTQSPPSLSASVGDRVTITCQASQDIGNSLGWYQRKPGDAPKLVIFDASDLETGVPS
7A5   AIRMTQSPPSLSASVGDRVTITCQASQDIGNSLGWYQQKPGKAPKLVIFDASDLETGVPS
       ****************************** *** ************************

7A5*  RFSGSGSGTDESLTISSLQPEDFATYYCQQGNSFPLTFGQGTRLEIK (SEQ ID NO: 10)
7A5   RFSGSGSGTDESLTISSLQPEDFATYYCQQGNSFPLTFGQGTRLEIK (SEQ ID NO: 35)
      ***********************************************
```

TABLE 3

HCVRs

```
11444*  QVQLVQSGAEVKKPGSSVKVSCKASGGTESSYAISWVRKAPGQGLEWMGLIIPSEDTAGY
11444   QVQLVQSGAEVKKPGSSVKVSCKASGGTESSYAISWVRQAPGQGLEWMGLIIPMEDTAGY
        **************************************:************* ******

11444*  AQEFQGRVAITVDESTSTAYMELSSLRSEDTAVYYCARAEHSSTGTEDYWGQGTLVTVSS
11444   AQKFQGRVAITVDESTSTAYMELSSLRSEDTAVYYCARAEHSSTGTEDYWGQGTLVTVSS
        **:*********************************************************

(SEQ ID NO: 16)
        (SEQ ID NO: 36)
```

TABLE 4

LCVRs

```
11444*  RIQMTQSPSSVSASVGDRVTITCRASQGISSWLAWYQDKPGKAPKLLISAASSLQSGVPS
11444   DIQMTQSPSSVSASVGDRVTITCRASQGISSWLAWYQKPGKAPKLLISAASSLQSGVPS
        ***********************************:************************

11444*  RFSGSGSGTDFTLTISSLQPEDFATYYCQQANHLPFTFGGGTKVEIK (SEQ ID NO: 22)
11444   RFSGSGSGTDFTLTISSLQPEDFATYYCQQANHLPFTFGGGTKVEIK (SEQ ID NO: 37)
        ***********************************************
```

TABLE 5

Heavy chain constant regions

```
7A5*     ASTKGPSVFPLAPCSKSTSGGTAALGCLVKDYFPEPVTVSWNSGALTSGVHTFPAVLQSS
Wt-IgG1  ASTKGPSVFPLAPSSKSTSGGTAALGCLVKDYFPEPVTVSWNSGALTSGVHTFPAVLQSS
11444*   ASTKGPSVFPLAPSSKSTSGGTAALGCLVKDYFPEPVTVSWNSGALTSGVATGPAVLQSS
         *************.****************************** * *******

7A5*     GLYSLSSVVTVPSSSLGTQTYICNVNHKPSNTKVDKRVEPDSGDKTHTCPPCPAPEAAGG
Wt-IgG1  GLYSLSSVVTVPSSSLGTQTYICNVNHKPSNTKVDKRVEPKSCDKTHTCPPCPAPELLGG
11444*   GLYSLSSVVTVPSSSLGTQTYICNVNHKPSNTKVDKRVEPKSCDKTHTCPPCPAPEAAGG
         ****************************************.* *************  **

7A5*     PSVFLFPPKPKDTLMISRTPEVTCVVVDVSHEDPEVKENWYVDGVEVHNAKTKPREEQYQ
Wt-IgG1  PSVFLFPPKPKDTLMISRTPEVTCVVVDVSHEDPEVKENWYVDGVEVHNAKTKPREEQYN
11444*   PSVFLFPPKPKDTLMISRTPEVTCVVVDVSHEDPEVKENWYVDGVEVHNAKTKPREEQYQ
         ***********************************************************:
```

TABLE 5-continued

Heavy chain constant regions

```
7A5*     STYRVVSVLTVLHQDWLNGKEYKCKVSNKALPAPIEKTISKAKGQPREPQVYTLPPSRGD
Wt-IgG1  STYRVVSVLTVLHQDWLNGKEYKCKVSNKALPAPIEKTISKAKGQPREPQVYTLPPSREE
11444*   STYRVVSVLTVLHQDWLNGKEYKCKVSNKALPAPIEKTISKAKGQPREPQVSTLPPSREE
         ******************************************** ******  :

7A5*     MTKNQVQLTCLVKGFYPSDIAVEWESNGQPENNYKTTPPVLDSDGSFFLASKLTVDKSRW
Wt-IgG1  MTKNQVSLTCLVKGFYPSDIAVEWESNGQPENNYKTTPPVLDSDGSFFLYSKLTVDKSRW
11444*   MTKNQVSLMCLVYGFYPSDIAVEWESNGQPENNYKTTPPVLDSDGSFFLYSVLTVDKSRW
         ******.* *** *********************************** * ********

7A5*     QQGNVFSCSVMHEALHNHYTQKSLSLSPGK  (SEQ ID NO: 30)
Wt-IgG1  QQGNVFSCSVMHEALHNHYTQKSLSLSPGK  (SEQ ID NO: 27)
11444*   QQGNVFSCSVMHEALHNHYTQKSLSLSPGK  (SEQ ID NO: 32)
         *****************************
```

TABLE 6 light chain constant regions

```
Wt-Lambda  GQPKAAPSVTLFPPSSEELQANKATLVCLISDFYPGAVTVAWKADSSPVKAGVETTTPSK
11444*     GQPKAAPSVTLFPPSSEELQANKATLVCYISDFYPGAVTVAWKADSSPVKAGVETTTPSK
           **************************** *******************************

Wt-Lambda  QSNNKYAASSYLSLTPEQWKSHRSYSCQVTHEGSTVEKTVAPTEC  (SEQ ID NO: 28)
11444*     QSNNKYAAWSYLSLTPEQWKSHRSYSCQVTHEGSTVEKTVAPTEC  (SEQ ID NO: 33)
           ******** ************************************
```

TABLE 7 light chain constant regions

```
Wt-Kappa  RTVAAPSVFIFPPSDEQLKSGTASVVCLLNNFYPREAKVQWKVDNALQSGNSQESVTEQD
7A5*      RTVAAPSVFIFPPSKEQLKSGTASVVCLLNNFYPREAKVQWKVDNALQSGNSQESVTEQD
          **************.*********************************************

Wt-Kappa  SKDSTYSLSSTLTLSKADYEKHKVYACEVTHQGLSSPVTKSENRGEC  (SEQ ID NO: 29)
7A5*      SKDSTYSLSSTLTLSKADYEKHKVYACEVTHQGLSSPVTKSENRGEC  (SEQ ID NO: 31)
          ***********************************************
```

TABLE 8

| Anti-CD137 Arm (7A5) | | Anti-PD-1 Arm (11444) | |
|---|---|---|---|
| Heavy chain | Light chain | Heavy chain | Light chain |
| Selective mutagenesis of residues for cognate heavy-light paring and heterodimerization | | | |
| Q39Y (Q39Y)[a] | A1D (A1D)[a] | Q39K (Q39K)[a] | D1R (D1R)[a] |
| S136C (S131C)[a] | Q38R (Q38R)[a] | K63E (K62E)[a] | Q38D (Q38D)[a] |
| K223D (K218D)[b] | K42D (K42D)[a] | H171A (H168A)[a] | L136Y (L135Y)[a] |
| C225G (C220G)[b] | D122K | F173G (F170G)[b] | S176W (S176W)[a] |
| E361G (E356G)[b] | (D122K)[a] | Y352S (Y349S)[b] | |
| E362D (E357D)[b] | | T369M (T366M)[b] | |
| S369Q (S364Q)[b] | | K373Y (K370Y)[b] | |
| Y412A (Y407A)[b] | | K412V (K409V)[b] | |
| Selective mutagenesis of residues for reducing FcγR and C1q binding | | | |
| L239A (L234A)[b] | | L237A (L234A)[b] | |
| L240A (L235A)[b] | | L238A (L235A)[b] | |
| N302Q (N297Q)[b] | | N300Q (N297Q)[b] | |

TABLE 8-continued

| Anti-CD137 Arm (7A5) | | Anti-PD-1 Arm (11444) | |
|---|---|---|---|
| Heavy chain | Light chain | Heavy chain | Light chain |
| Other selective mutagenesis of residues[c] | | | |
| M101A (M97A)[a] | | M54S (M53S)[a] | |
| G106A (G101A)[a] | | | |

[a]Numbering in parentheses is based on Kabat numbering (Kabat EA et al., 1991 *Sequences of Proteins of Immunological Interest*, 5th Ed, Public Health Service, National Institutes of Health, Bethesda, MD).
[b]Numbering in parentheses is based on EU numbering (Kabat EA et al., 1991 *Sequences of Proteins of Immunological Interest*, 5th Ed, Public Health Service, National Institutes of Health, Bethesda, MD).
[c]Selective mutagenesis of M101A and G106A in the 7A5 heavy chain was performed to eliminate methionine oxidation and reduce the binding affinity of the human CD137 agonistic arm of the bispecific antibody. The binding affinity of Antibody A to human PD-1 is at least 10-fold higher than that of Antibody A's binding affinity to human CD137, preferably more than 100-fold higher. The selective mutagenesis of M45S in the 11444 heavy chain was also performed to eliminate methionine oxidation.

The antibodies of the present invention are heterodimeric in that each arm of the antibody exhibits selective monovalent binding to its cognate antigen due in part to two different heavy chains and the two different light chains. In the present invention, one arm of the antibody binds human PD-1 (SEQ ID NO:25) while the other arm binds human CD137 (SEQ ID NO:26). The antibodies of the present invention demonstrate favorable pharmacological properties due in part to fact that said bispecific antibodies display a binding affinity to human PD-1 (SEQ ID NO:25) that is at least 10-fold higher than to human CD137 (SEQ ID NO:26), preferably, more than 100-fold higher. Thus, the antibodies of the present invention selectively target PD-1 expressing cells and potentially limit the CD137 agonism to those cells that co-express PD-1. Moreover, the antibodies of the present invention retain the functionality of promoting interferon gamma (IFNγ) production in a human peripheral blood mononuclear cell (PBMC) co-stimulation assay, as compared to a combination of the parental antibodies. Furthermore, the antibodies described herein unexpectedly induce a unique immune-gene expression pattern in H292 tumor tissue when the antibody is adminstered to mice as compared to a combination of the parental monoclonal antibodies.

Accordingly, the present invention provides an antibody that antagonizes human PD-1 (SEQ ID NO:25) and agonizes human CD137 (SEQ ID NO:26), wherein the binding affinity to human PD-1 is at least 10-fold higher than that to human CD137. The present invention provides an antibody that antagonizes human PD-1 (SEQ ID NO:25) and agonizes human CD137 (SEQ ID NO:26), wherein the binding affinity to human PD-1 is 100-fold higher than that to human CD137.

The present invention also provides an antibody that antagonizes human PD-1 (SEQ ID NO:25 and agonizes human CD137 (SEQ ID NO:26) at a level that is less than the level of CD137 agonism by BMS20H4.9, as measured in the Jurkat NFκB-Luc reporter assay disclosed herein in cells engineered to co-express both CD137 and PD-1.

The present invention also provides an antibody that antagonizes human PD-1 (SEQ ID NO:25) and agonizes human CD137 (SEQ ID NO:26), wherein the first heavy chain of the antibody forms at least one disulfide bond with the first light chain of the antibody, the second heavy chain of the antibody forms at least one disulfide bond with the second light chain of the antibody, and the first heavy chain of the antibody forms at least one disulfide bond with the second heavy chain of the antibody; optionally wherein the binding affinity of the antibody to human PD-1 is 10-fold or higher than to human CD137, preferably wherein the binding affinity of the antibody to human PD-1 is 100-fold or higher than to human CD137.

The present invention provides an antibody that antagonizes human PD-1 (SEQ ID NO:25) and agonizes human CD137 (SEQ ID NO:26), comprising a first and second heavy chain and a first and second light chain, wherein each chain comprises a variable region and a constant region, and wherein:
 a) the first heavy chain of the antibody comprises a complementarity-determining region 1 (CDR1) having the amino acid sequence of SEQ ID NO:1, a complementarity-determining region 2 (CDR2) having the amino acid sequence of SEQ ID NO:2, and a complementarity-determining region (CDR3) having the amino acid sequence of SEQ ID NO:3;
 b) the first light chain of the antibody comprises a CDR1 having the amino acid sequence of SEQ ID NO:7, a CDR2 having the amino acid sequence of SEQ ID NO:8, and a CDR3 having the amino acid sequence of SEQ ID NO:9;
 c) the second heavy chain of the antibody comprises a CDR1 having the amino acid sequence of SEQ ID NO:13, a CDR2 having the amino acid sequence of SEQ ID NO:14, and a CDR3 having the amino acid sequence of SEQ ID NO:15; and
 d) the second light chain of the antibody comprises a CDR1 having the amino acid sequence of SEQ ID NO:19, a CDR2 having the amino acid sequence of SEQ ID NO:20, and a CDR3 having the amino acid sequence of SEQ ID NO:21.

The present invention provides an antibody comprising a first and second heavy chain and a first and second light chain, wherein each chain comprises a variable region and a constant region, and wherein:
 a) the variable region of the first heavy chain has the amino acid sequence of SEQ ID NO:4;
 b) the variable region of the first light chain has the amino acid sequence of SEQ ID NO:10;
 c) the variable region of the second heavy chain has the amino acid sequence of SEQ ID NO:16; and
 d) the variable region of the second light chain has the amino acid sequence of SEQ ID NO:22.

The present invention provides an antibody comprising a first and second heavy chain and a first and second light chain, wherein:
 a) the first heavy chain has the amino acid sequence of SEQ ID NO:5;
 b) the first light chain has the amino acid sequence of SEQ ID NO: 11;
 c) the second heavy chain has the amino acid sequence of SEQ ID NO: 17; and
 d) the second light chain has the amino acid sequence of SEQ ID NO:23.

The present invention provides an antibody comprising a first and second heavy chain and a first and second light chain, wherein the first heavy chain of the antibody forms at least one disulfide bond with the first light chain of the antibody, the second heavy chain of the antibody forms at least one disulfide bond with the second light chain of the antibody, and the first heavy chain of the antibody forms at least one disulfide bond with the second heavy chain of the antibody.

The present invention provides an antibody disclosed herein, wherein the antibody is a human IgG1 engineered to reduce the binding of the antibody to an Fc gamma receptor.

The present invention provides a DNA molecule comprising a polynucleotide encoding for at least one polypeptide having the amino acid sequence of SEQ ID NO:5, the amino acid sequence of SEQ ID NO:11, the amino acid sequence of SEQ ID NO:17, and the amino acid sequence of SEQ ID NO:23.

The present invention provides a mammalian cell comprising a DNA molecule comprising a polynucleotide encoding for at least one polypeptide having the amino acid sequence of SEQ ID NO:5, the amino acid sequence of SEQ ID NO:11, the amino acid sequence of SEQ ID NO:17, and the amino acid sequence of SEQ ID NO:23.

The present invention provides a process for producing an antibody comprising cultivating a mammalian cell capable of expressing the antibody and recovering the antibody; wherein the antibody comprises a first and second heavy chain and a first and second light chain, wherein each chain comprises a variable region and a constant region, and wherein:
 a) the first heavy chain of the antibody comprises a CDR1 having the amino acid sequence of SEQ ID NO:1, a CDR2 having the amino acid sequence of SEQ ID NO:2, and a CDR3 having the amino acid sequence of SEQ ID NO:3;

b) the first light chain of the antibody comprises a CDR1 having the amino acid sequence of SEQ ID NO:7, a CDR2 having the amino acid sequence of SEQ ID NO:8, and a CDR3 having the amino acid sequence of SEQ ID NO:9;
c) the second heavy chain of the antibody comprises a CDR1 having the amino acid sequence of SEQ ID NO:13, a CDR2 having the amino acid sequence of SEQ ID NO:14, and a CDR3 having the amino acid sequence of SEQ ID NO:15; and
d) the second light chain of the antibody comprises a CDR1 having the amino acid sequence of SEQ ID NO:19, a CDR2 having the amino acid sequence of SEQ ID NO:20, and a CDR3 having the amino acid sequence of SEQ ID NO:21; optionally, wherein the first heavy chain of the antibody forms at least one disulfide bond with the first light chain of the antibody, the second heavy chain of the antibody forms at least one disulfide bond with the second light chain of the antibody, and the first heavy chain of the antibody forms at least one disulfide bond with the second heavy chain of the antibody.

The present invention provides a process for producing an antibody comprising cultivating a mammalian cell capable of expressing the antibody and recovering the antibody; wherein the antibody comprises a first and second heavy chain and a first and second light chain, wherein each chain comprises a variable region and a constant region, and wherein:
a) the variable region of the first heavy chain has the amino acid sequence of SEQ ID NO:4;
b) the variable region of the first light chain has the amino acid sequence of SEQ ID NO:10;
c) the variable region of the second heavy chain has the amino acid sequence of SEQ ID NO:16; and
d) the variable region of the second light chain has the amino acid sequence of SEQ ID NO:22.

The present invention provides a process for producing an antibody comprising cultivating a mammalian cell capable of expressing the antibody and recovering the antibody; wherein the antibody comprises a first and second heavy chain and a first and second light chain, and wherein:
a) the first heavy chain has the amino acid sequence of SEQ ID NO:5;
b) the first light chain has the amino acid sequence of SEQ ID NO: 11;
c) the second heavy chain has the amino acid sequence of SEQ ID NO: 17; and
d) the second light chain has the amino acid sequence of SEQ ID NO:23.

The present invention provides a process for producing an antibody of the present invention disclosed herein comprising cultivating a mammalian cell capable of expressing the antibody and recovering the antibody; wherein the antibody is a human IgG1 engineered to reduce the binding of the antibody to an Fc gamma receptor.

The present invention provides an antibody produced by a process comprising cultivating a mammalian cell capable of expressing the antibody and recovering the antibody; wherein the antibody comprises a first and second heavy chain and a first and second light chain, wherein each chain comprises a variable region and a constant region, and wherein:
a) the first heavy chain of the antibody comprises a CDR1 having the amino acid sequence of SEQ ID NO:1, a CDR2 having the amino acid sequence of SEQ ID NO:2, and a CDR3 having the amino acid sequence of SEQ ID NO:3;
b) the first light chain of the antibody comprises a CDR1 having the amino acid sequence of SEQ ID NO:7, a CDR2 having the amino acid sequence of SEQ ID NO:8, and a CDR3 having the amino acid sequence of SEQ ID NO:9;
c) the second heavy chain of the antibody comprises a CDR1 having the amino acid sequence of SEQ ID NO:13, a CDR2 having the amino acid sequence of SEQ ID NO:14, and a CDR3 having the amino acid sequence of SEQ ID NO: 15; and
d) the second light chain of the antibody comprises a CDR1 having the amino acid sequence of SEQ ID NO:19, a CDR2 having the amino acid sequence of SEQ ID NO:20, and a CDR3 having the amino acid sequence of SEQ ID NO:21; optionally, wherein the first heavy chain of the antibody forms at least one disulfide bond with the first light chain of the antibody, the second heavy chain of the antibody forms at least one disulfide bond with the second light chain of the antibody, and the first heavy chain of the antibody forms at least one disulfide bond with the second heavy chain of the antibody.

The present invention provides an antibody produced by a process comprising cultivating a mammalian cell capable of expressing the antibody and recovering the antibody; wherein the antibody comprising a first and second heavy chain and a first and second light chain, wherein each chain comprises a variable region and a constant region, and wherein:
a) the variable region of the first heavy chain has the amino acid sequence of SEQ ID NO:4;
b) the variable region of the first light chain has the amino acid sequence of SEQ ID NO:10;
c) the variable region of the second heavy chain has the amino acid sequence of SEQ ID NO:16; and
d) the variable region of the second light chain has the amino acid sequence of SEQ ID NO:22.

The present invention provides an antibody produced by a process comprising cultivating a mammalian cell capable of expressing the antibody and recovering the antibody; wherein the antibody comprises a first and second heavy chain and a first and second light chain, and wherein:
a) the first heavy chain has the amino acid sequence of SEQ ID NO:5;
b) the first light chain has the amino acid sequence of SEQ ID NO: 11;
c) the second heavy chain has the amino acid sequence of SEQ ID NO: 17; and
d) the second light chain has the amino acid sequence of SEQ ID NO:23.

The present invention provides a pharmaceutical composition comprising an antibody, wherein the antibody antagonizes human PD-1 (SEQ ID NO:25) and agonizes human CD137 (SEQ ID NO:26), and the antibody comprises a first and second heavy chain and a first and second light chain, wherein each chain comprises a variable region and a constant region, and wherein:
a) the first heavy chain of the antibody comprises a CDR1 having the amino acid sequence of SEQ ID NO:1, a CDR2 having the amino acid sequence of SEQ ID NO:2, and a CDR3 having the amino acid sequence of SEQ ID NO:3;
b) the first light chain of the antibody comprises a CDR1 having the amino acid sequence of SEQ ID NO:7, a CDR2 having the amino acid sequence of SEQ ID NO:8, and a CDR3 having the amino acid sequence of SEQ ID NO:9;
c) the second heavy chain of the antibody comprises a CDR1 having the amino acid sequence of SEQ ID NO:13, a CDR2 having the amino acid sequence of SEQ ID NO:14, and a CDR3 having the amino acid sequence of SEQ ID NO:15; and
d) the second light chain of the antibody comprises a CDR1 having the amino acid sequence of SEQ ID NO:19, a CDR2 having the amino acid sequence of SEQ ID NO:20, and a CDR3 having the amino acid sequence of SEQ ID NO:21; and wherein the first heavy chain of the antibody forms at least one disulfide bond with the first light chain of the antibody, the second heavy chain of the antibody forms at least one disulfide bond with the second light chain of the antibody, and the first heavy chain of the antibody forms at least one disulfide bond with the second heavy chain of the antibody.

The present invention provides a pharmaceutical composition comprising an antibody, wherein the antibody comprises a first and second heavy chain and a first and second light chain, wherein each chain comprises a variable region and a constant region, and wherein:
a) the variable region of the first heavy chain has the amino acid sequence of SEQ ID NO:4;
b) the variable region of the first light chain has the amino acid sequence of SEQ ID NO:10;
c) the variable region of the second heavy chain has the amino acid sequence of SEQ ID NO:16; and
d) the variable region of the second light chain has the amino acid sequence of SEQ ID NO:22.

The present invention provides a pharmaceutical composition comprising an antibody, wherein the antibody comprises a first and second heavy chain and a first and second light chain, wherein:
a) the first heavy chain has the amino acid sequence of SEQ ID NO:5;
b) the first light chain has the amino acid sequence of SEQ ID NO: 11;
c) the second heavy chain has the amino acid sequence of SEQ ID NO: 17; and
d) the second light chain has the amino acid sequence of SEQ ID NO:23.

The present invention provides a pharmaceutical composition comprising an antibody of the present invention, wherein the antibody is a human IgG1 engineered to reduce the binding of the antibody to an Fc gamma receptor.

The present invention provides a method of treating cancer comprising administering to a human patient in need thereof, an effective amount of an antibody, wherein the antibody antagonizes human PD-1 (SEQ ID NO:25) and agonizes human CD137 (SEQ ID NO:26), and the antibody comprises a first and second heavy chain and a first and second light chain, wherein each chain comprises a variable region and a constant region, and wherein:
a) the first heavy chain of the antibody comprises a CDR1 having the amino acid sequence of SEQ ID NO:1, a CDR2 having the amino acid sequence of SEQ ID NO:2, and a CDR3 having the amino acid sequence of SEQ ID NO:3;
b) the first light chain of the antibody comprises a CDR1 having the amino acid sequence of SEQ ID NO:7, a CDR2 having the amino acid sequence of SEQ ID NO:8, and a CDR3 having the amino acid sequence of SEQ ID NO:9;
c) the second heavy chain of the antibody comprises a CDR1 having the amino acid sequence of SEQ ID NO:13, a CDR2 having the amino acid sequence of SEQ ID NO:14, and a CDR3 having the amino acid sequence of SEQ ID NO:15; and
d) the second light chain of the antibody comprises a CDR1 having the amino acid sequence of SEQ ID NO:19, a CDR2 having the amino acid sequence of SEQ ID NO:20, and a CDR3 having the amino acid sequence of SEQ ID NO:21; and wherein:
the first heavy chain of the antibody forms at least one disulfide bond with the first light chain of the antibody, the second heavy chain of the antibody forms at least one disulfide bond with the second light chain of the antibody, and the first heavy chain of the antibody forms at least one disulfide bond with the second heavy chain of the antibody.

The present invention provides a method of treating cancer comprising administering to a human patient in need thereof, an effective amount of an antibody, wherein the antibody comprises a first and second heavy chain and a first and second light chain, wherein each chain comprises a variable region and a constant region, and wherein:
a) the variable region of the first heavy chain has the amino acid sequence of SEQ ID NO:4;
b) the variable region of the first light chain has the amino acid sequence of SEQ ID NO:10;
c) the variable region of the second heavy chain has the amino acid sequence of SEQ ID NO:16; and
d) the variable region of the second light chain has the amino acid sequence of SEQ ID NO:22.

The present invention provides a method of treating cancer comprising administering to a human patient in need thereof, an effective amount of an antibody, wherein the antibody comprises a first and second heavy chain and a first and second light chain, wherein:
a) the first heavy chain has the amino acid sequence of SEQ ID NO:5;
b) the first light chain has the amino acid sequence of SEQ ID NO: 11;
c) the second heavy chain has the amino acid sequence of SEQ ID NO: 17; and
d) the second light chain has the amino acid sequence of SEQ ID NO:23.

The present invention provides a method of treating cancer comprising administering to a human patient in need thereof, an effective amount of an antibody described herein, wherein the antibody is a human IgG1 engineered to reduce the binding of the antibody to an Fe gamma receptor.

The present invention provides a method of treating cancer comprising administering to a human patient in need thereof, an effective amount of an antibody described herein, wherein the cancer is melanoma, non-small cell lung cancer, small cell lung cancer, head and neck cancer, liver cancer, colorectal cancer, pancreatic cancer, gastric cancer, kidney cancer, bladder cancer, prostate cancer, breast cancer, ovarian cancer, endometrial cancer, esophageal cancer, soft tissue sarcoma, cholangiocarcinoma, thyroid cancer, hepatocellular carcinoma, or mesothelioma.

The present invention provides a method of treating cancer comprising administering to a human patient in need thereof, an effective amount of an antibody described herein, wherein the antibody is administered in combination with ionizing radiation.

The present invention provides a method of treating cancer comprising administering to a human patient in need thereof, an effective amount of an antibody described herein, wherein the antibody is administered in combination with one or more chemotherapeutic agents.

The present invention provides a method of treating cancer comprising administering to a human patient in need thereof, an effective amount of an antibody described herein, wherein the antibody is administered in combination with ionizing radiation and one or more chemotherapeutic agents.

The present invention provides an antibody for use in treating cancer, wherein the antibody antagonizes human PD-1 (SEQ ID NO:25) and agonizes human CD137 (SEQ ID NO:26), and the antibody comprises a first and second heavy chain and a first and second light chain, wherein each chain comprises a variable region and a constant region, and wherein:
   a) the first heavy chain of the antibody comprises a CDR1 having the amino acid sequence of SEQ ID NO:1, a CDR2 having the amino acid sequence of SEQ ID NO:2, and a CDR3 having the amino acid sequence of SEQ ID NO:3;
   b) the first light chain of the antibody comprises a CDR1 having the amino acid sequence of SEQ ID NO:7, a CDR2 having the amino acid sequence of SEQ ID NO:8, and a CDR3 having the amino acid sequence of SEQ ID NO:9;
   c) the second heavy chain of the antibody comprises a CDR1 having the amino acid sequence of SEQ ID NO:13, a CDR2 having the amino acid sequence of SEQ ID NO:14, and a CDR3 having the amino acid sequence of SEQ ID NO:15; and
   d) the second light chain of the antibody comprises a CDR1 having the amino acid sequence of SEQ ID NO:19, a CDR2 having the amino acid sequence of SEQ ID NO:20, and a CDR3 having the amino acid sequence of SEQ ID NO:21; and wherein:
      the first heavy chain of the antibody forms at least one disulfide bond with the first light chain of the antibody, the second heavy chain of the antibody forms at least one disulfide bond with the second light chain of the antibody, and the first heavy chain of the antibody forms at least one disulfide bond with the second heavy chain of the antibody.

The present invention provides an antibody of the present invention for use in treating cancer, wherein the antibody comprises a first and second heavy chain and a first and second light chain, wherein each chain comprises a variable region and a constant region, and wherein:
   a) the variable region of the first heavy chain has the amino acid sequence of SEQ ID NO:4;
   b) the variable region of the first light chain has the amino acid sequence of SEQ ID NO:10;
   c) the variable region of the second heavy chain has the amino acid sequence of SEQ ID NO:16; and
   d) the variable region of the second light chain has the amino acid sequence of SEQ ID NO:22.

The present invention provides an antibody of the present invention for use in treating cancer, wherein the antibody comprises a first and second heavy chain and a first and second light chain wherein:
   a) the first heavy chain has the amino acid sequence of SEQ ID NO:5;
   b) the first light chain has the amino acid sequence of SEQ ID NO: 11;
   c) the second heavy chain has the amino acid sequence of SEQ ID NO: 17; and
   d) the second light chain has the amino acid sequence of SEQ ID NO:23.

The present invention provides an antibody of the present invention for use in treating cancer, wherein the antibody is a human IgG1 engineered to reduce the binding of the antibody to an Fc gamma receptor.

The present invention provides an antibody of the present invention for use in treating cancer, wherein the cancer is melanoma, non-small cell lung cancer, small cell lung cancer, head and neck cancer, liver cancer, colorectal cancer, pancreatic cancer, gastric cancer, kidney cancer, bladder cancer, prostate cancer, breast cancer, ovarian cancer, endometrial cancer, esophageal cancer, soft tissue sarcoma, cholangiocarcinoma, thyroid cancer, hepatocellular carcinoma, or mesothelioma.

The present invention provides an antibody of the present invention for use in treating cancer, wherein the antibody is administered in simultaneous, separate, or sequential combination with ionizing radiation.

The present invention provides an antibody of the present invention for use in treating cancer, wherein the antibody is administered in simultaneous, separate, or sequential combination with one or more chemotherapeutic agents.

The present invention provides an antibody of the present invention for use in treating cancer, wherein the antibody is administered in simultaneous, separate, or sequential combination with ionizing radiation and one or more chemotherapeutic agents.

The present invention provides a pharmaceutical composition comprising an antibody for use in treating cancer, wherein the antibody antagonizes human PD-1 (SEQ ID NO:25) and agonizes human CD137 (SEQ ID NO:26), and the antibody comprises a first and second heavy chain and a first and second light chain, wherein each chain comprises a variable region and a constant region, and wherein:
   a) the first heavy chain of the antibody comprises a CDR1 having the amino acid sequence of SEQ ID NO:1, a CDR2 having the amino acid sequence of SEQ ID NO:2, and a CDR3 having the amino acid sequence of SEQ ID NO:3;
   b) the first light chain of the antibody comprises a CDR1 having the amino acid sequence of SEQ ID NO:7, a CDR2 having the amino acid sequence of SEQ ID NO:8, and a CDR3 having the amino acid sequence of SEQ ID NO:9;
   c) the second heavy chain of the antibody comprises a CDR1 having the amino acid sequence of SEQ ID NO:13, a CDR2 having the amino acid sequence of SEQ ID NO:14, and a CDR3 having the amino acid sequence of SEQ ID NO:15; and
   d) the second light chain of the antibody comprises a CDR1 having the amino acid sequence of SEQ ID NO:19, a CDR2 having the amino acid sequence of SEQ ID NO:20, and a CDR3 having the amino acid sequence of SEQ ID NO:21; and wherein:
      the first heavy chain of the antibody forms at least one disulfide bond with the first light chain of the antibody, the second heavy chain of the antibody forms at least one disulfide bond with the second light chain of the antibody, and the first heavy chain of the antibody forms at least one disulfide bond with the second heavy chain of the antibody The present invention provides a pharmaceutical composition comprising an antibody for use in treating cancer, wherein the antibody comprises a first and second heavy chain and a first and second light chain, wherein each chain comprises a variable region and a constant region, and wherein:

a) the variable region of the first heavy chain has the amino acid sequence of SEQ ID NO:4;
b) the variable region of the first light chain has the amino acid sequence of SEQ ID NO:10;
c) the variable region of the second heavy chain has the amino acid sequence of SEQ ID NO:16; and
d) the variable region of the second light chain has the amino acid sequence of SEQ ID NO:22.

The present invention provides a pharmaceutical composition comprising an antibody for use in treating cancer, wherein the antibody comprises a first and second heavy chain and a first and second light chain, wherein:
a) the first heavy chain has the amino acid sequence of SEQ ID NO:5;
b) the first light chain has the amino acid sequence of SEQ ID NO: 11;
c) the second heavy chain has the amino acid sequence of SEQ ID NO: 17; and
d) the second light chain has the amino acid sequence of SEQ ID NO:23.

The present invention provides a pharmaceutical composition comprising an antibody of the present invention for use in treating cancer, wherein the antibody is a human IgG1 engineered to reduce the binding of the antibody to an Fc gamma receptor.

The present invention provides a pharmaceutical composition comprising an antibody of the present invention for use in treating cancer, wherein the cancer is melanoma, non-small cell lung cancer, small cell lung cancer, head and neck cancer, liver cancer, colorectal cancer, pancreatic cancer, gastric cancer, kidney cancer, bladder cancer, prostate cancer, breast cancer, ovarian cancer, endometrial cancer, esophageal cancer, soft tissue sarcoma, cholangiocarcinoma, thyroid cancer, hepatocellular carcinoma, or mesothelioma.

The present invention provides a pharmaceutical composition comprising an antibody of the present invention for use in treating cancer, wherein the composition is administered in simultaneous, separate, or sequential combination with ionizing radiation.

The present invention provides a pharmaceutical composition comprising an antibody of the present invention for use in treating cancer, wherein the pharmaceutical composition is administered in simultaneous, separate, or sequential combination with one or more chemotherapeutic agents.

The present invention provides a pharmaceutical composition comprising an antibody of the present invention for use in treating cancer, wherein the pharmaceutical composition is administered in simultaneous, separate, or sequential combination with ionizing radiation and one or more chemotherapeutic agents.

The present invention provides the use of an antibody of the present invention in the manufacture of a medicament for treating cancer, wherein the antibody antagonizes human PD-1 (SEQ ID NO:25) and agonizes human CD137 (SEQ ID NO:26), and the antibody comprises a first and second heavy chain and a first and second light chain, wherein each chain comprises a variable region and a constant region, and wherein:
a) the first heavy chain of the antibody comprises a CDR1 having the amino acid sequence of SEQ ID NO:1, a CDR2 having the amino acid sequence of SEQ ID NO:2, and a CDR3 having the amino acid sequence of SEQ ID NO:3;
b) the first light chain of the antibody comprises a CDR1 having the amino acid sequence of SEQ ID NO:7, a CDR2 having the amino acid sequence of SEQ ID NO:8, and a CDR3 having the amino acid sequence of SEQ ID NO:9;
c) the second heavy chain of the antibody comprises a CDR1 having the amino acid sequence of SEQ ID NO:13, a CDR2 having the amino acid sequence of SEQ ID NO:14, and a CDR3 having the amino acid sequence of SEQ ID NO:15; and
d) the second light chain of the antibody comprises a CDR1 having the amino acid sequence of SEQ ID NO:19, a CDR2 having the amino acid sequence of SEQ ID NO:20, and a CDR3 having the amino acid sequence of SEQ ID NO:21; and wherein:
the first heavy chain of the antibody forms at least one disulfide bond with the first light chain of the antibody, the second heavy chain of the antibody forms at least one disulfide bond with the second light chain of the antibody, and the first heavy chain of the antibody forms at least one disulfide bond with the second heavy chain of the antibody.

The present invention provides the use of an antibody of the present invention in the manufacture of a medicament for treating cancer, wherein the antibody comprises a first and second heavy chain and a first and second light chain, wherein each chain comprises a variable region and a constant region, and wherein:
a) the variable region of the first heavy chain has the amino acid sequence of SEQ ID NO:4;
b) the variable region of the first light chain has the amino acid sequence of SEQ ID NO:10;
c) the variable region of the second heavy chain has the amino acid sequence of SEQ ID NO:16; and
d) the variable region of the second light chain has the amino acid sequence of SEQ ID NO:22.

The present invention provides the use of an antibody of the present invention in the manufacture of a medicament for treating cancer, wherein the antibody comprises a first and second heavy chain and a first and second light chain, wherein:
a) the first heavy chain has the amino acid sequence of SEQ ID NO:5;
b) the first light chain has the amino acid sequence of SEQ ID NO: 11;
c) the second heavy chain has the amino acid sequence of SEQ ID NO: 17; and
d) the second light chain has the amino acid sequence of SEQ ID NO:23.

The present invention provides the use of an antibody of the present invention in the manufacture of a medicament for treating cancer, wherein the antibody is a human IgG1 engineered to reduce the binding of the antibody to an Fc gamma receptor.

The present invention provides the use of an antibody of the present invention in the manufacture of a medicament for treating cancer, wherein the cancer is melanoma, non-small cell lung cancer, small cell lung cancer, head and neck cancer, liver cancer, colorectal cancer, pancreatic cancer, gastric cancer, kidney cancer, bladder cancer, prostate cancer, breast cancer, ovarian cancer, endometrial cancer, esophageal cancer, soft tissue sarcoma, cholangiocarcinoma, thyroid cancer, hepatocellular carcinoma, or mesothelioma.

The present invention provides the use of an antibody of the present invention in the manufacture of a medicament for treating cancer, wherein the antibody is administered in simultaneous, separate, or sequential combination with ionizing radiation.

The present invention provides the use of an antibody of the present invention in the manufacture of a medicament for treating cancer, wherein the antibody is administered in simultaneous, separate, or sequential combination with one or more chemotherapeutic agents.

The present invention provides the use of an antibody of the present invention in the manufacture of a medicament for treating cancer, wherein the antibody is administered in simultaneous, separate, or sequential combination with ionizing radiation and one or more chemotherapeutic agents.

In embodiments that refer to a method of treatment as described herein, such embodiments are also further embodiments for use in that treatment, or alternatively for the use in the manufacture of a medicament for use in that treatment.

Non-limiting examples of useful chemotherapeutic agents include 5-fluorouracil, hydroxyurea, gemcitabine, methotrexate, doxorubicin, etoposide, carboplatin, cisplatin, cyclophosphamide, melphalan, dacarbazine, taxol, camptothecin, FOLFIRI, FOLFOX, docetaxel, daunorubicin, paclitaxel, oxaliplatin, and combinations thereof.

The antibodies of the present invention, or pharmaceutical compositions comprising the same, may be administered by parenteral routes, a non-limiting example of which is intravenous administration. The antibodies of the present invention may be administered to a human patient alone with pharmaceutically acceptable carriers, diluents, or excipients in single or multiple doses. A pharmaceutical composition of the present invention may be prepared by methods known in the art (e.g., *Remington: The Science and Practice of Pharmacy*, $22^{nd}$ ed. (2012), A. Loyd et al., Pharmaceutical Press).

Dosage regimens may be adjusted to provide the optimum desired response (e.g., a therapeutic effect). Dosing schedules, for intravenous (i.v.) or non-intravenous administration, localized or systemic, or combinations thereof, typically range from a single bolus dosage or continuous infusion to multiple administrations per day (e.g., every 4-6 hours), or as indicated by a treating physician and the patient's condition.

As used herein, the term "antagonize" refers to the act of blocking, interrupting, suppressing, or reducing a desired biological activity. In this regard, the antibodies of the present invention antagonize human PD-1 by binding to human PD-1 and blocking the binding of human PD-L1 to human PD-1.

As used herein, the term "agonize" refers to the act of stimulating, promoting, activating, or enhancing a desired biological activity. In this regard, the antibodies of the present invention agonize human CD137 by binding to human CD137 and activating signal transduction pathways downstream of CD137 independently of the natural human ligand to CD137.

The term "treating" (or "treat" or "treatment") refers to slowing, interrupting, arresting, alleviating, stopping, reducing, or reversing the progression or severity of an existing symptom, disorder, condition, or disease.

"Effective amount" means the amount of an antibody of the present invention or a pharmaceutical composition comprising an antibody of the present invention that elicits the biological or medical response or desired therapeutic effect on a tissue, system, animal, mammal or human that is being sought by the researcher, medical doctor, or other clinician. An effective amount of the antibody may vary according to factors such as the disease state, age, sex, and weight of the individual, and the ability of the antibody to elicit a desired response in the individual. An effective amount is also one in which any toxic or detrimental effect of the antibody is outweighed by the therapeutically beneficial effects.

The term "antibody" as used herein refers to an engineered, non-naturally occurring-polypeptide complex having two heavy chains and two light chains such that the heavy chains and lights chains are interconnected by disulfide bonds; wherein the antibody is an IgG-like antibody. Each heavy chain is comprised of an N-terminal HCVR (heavy chain variable region) and a heavy chain constant region. Each light chain is comprised of an N-terminal LCVR (light chain variable region) and a light chain constant region. The constant region of the heavy chains contain CH1, CH2, and CH3 domains.

The term "modified human IgG1" as used herein means a human IgG1 engineered to reduce the binding of the human IgG1 to at least one human Fc gamma receptor. Typically this is performed by mutating residues that lead to a reduction in the binding of the antibody to the Fc gamma receptor(s).

The HCVR and LCVR regions can be further subdivided into regions of hyper-variability, termed complementarity determining regions ("CDRs"), interspersed with regions that are more conserved, termed framework regions ("FRs"). Each HCVR and LCVR is composed of three CDRs and four FRs, arranged from the amino-terminus to the carboxy-terminus in the following order: FR1, CDR1, FR2, CDR2, FR3, CDR3, FR4. Herein, the three CDRs of the heavy chain are referred to as "HCDR1, HCDR2, and HCDR3" and the three CDRs of the light chain are referred to as "LCDR1, LCDR2 and LCDR3". The CDRs contain most of the residues which form specific interactions with the antigen. For the purposes of the present invention, the North CDR definitions are used. The North CDR definition (North et al., "A New Clustering of Antibody CDR Loop Conformations", Journal of Molecular Biology, 406, 228-256 (2011)) is based on affinity propagation clustering with a large number of crystal structures.

A DNA molecule of the present invention is a DNA molecule that comprises a non-naturally occurring polynucleotide sequence encoding a polypeptide having the amino acid sequence of at least one of the polypeptides in an antibody of the present invention.

An isolated DNA molecule encoding a HCVR region may be converted to a full-length heavy chain gene by operably linking the HCVR-encoding DNA to another DNA molecule encoding heavy chain constant regions. The sequences of human, as well as other mammalian, heavy chain constant region genes are known in the art. DNA fragments encompassing these regions may be obtained, e.g., by standard PCR amplification.

An isolated DNA encoding a LCVR region may be converted to a full-length light chain gene by operably linking the LCVR-encoding DNA to another DNA molecule encoding a light chain constant region. The sequences of human, as well as other mammalian, light chain constant region genes are known in the art. DNA fragments encompassing these regions may be obtained by standard PCR amplification.

The polynucleotides of the present invention may be expressed in a host cell after the sequences are operably linked to an expression control sequence. The expression vectors are typically replicable in the host organisms either as episomes or as an integral part of the host chromosomal DNA. Commonly, expression vectors contain selection markers, e.g., tetracycline, neomycin, and dihydrofolate reductase, to permit detection of those cells transformed with the desired DNA sequences.

An expression vector containing the polynucleotide sequences of interest (e.g., the polynucleotides encoding the polypeptides of an antibody and expression control sequences) can be transferred into a host cell by known methods, which vary depending on the type of host cells.

An antibody of the present invention may readily be produced in mammalian host cells, non-limiting examples of which includes CHO, NS0, HEK293 or COS cells. The host cells may be cultured using techniques known in the art.

Various methods of protein purification may be employed to purify an antibody of the present invention and such methods are known in the art and described, for example, in Deutscher, *Methods in Enzymology* 182: 83-89 (1990) and Scopes, *Protein Purification: Principles and Practice*, 3rd Edition, Springer, N.Y. (1994).

Antibody Expression and Purification

The amino acid sequences of the variable regions of the heavy and light chains and the full-length heavy and light chains of Antibody A and the nucleotide sequences encoding the full-length heavy and light chains of Antibody A, are listed in the section entitled "Amino Acid and Nucleotide Sequences." In addition, the SEQ ID NOs for the CDRs, the variable regions, the constant regions, the full-length heavy and light chains and the nucleotide sequences encoding the full-length heavy and light chains of Antibody A are shown in Table 9.

TABLE 9

| | Anti-CD137 Arm (7A5*) | Anti-PD-1 Arm (11444*) | Parental antibody 7A5 | Parental antibody 11444 |
|---|---|---|---|---|
| HCDR1 | 1 | 13 | | |
| HCDR2 | 2 | 14 | | |
| HCDR3 | 3 | 15 | | |
| LCDR1 | 7 | 19 | | |
| LCDR2 | 8 | 20 | | |
| LCDR3 | 9 | 21 | | |
| HCVR | 4 | 16 | 34 | 36 |
| LCVR | 10 | 22 | 35 | 37 |
| HCCR | 30 | 32 | | |
| LCCR | 31 | 33 | | |
| Heavy chain | 5 | 17 | | |
| Light chain | 11 | 23 | | |
| DNA Heavy Chain | 6 | 18 | | |
| DNA Light Chain | 12 | 24 | | |

HCCR: Heavy chain constant region;
LCCR: Light chain constant region

The antibodies of the present invention may be expressed and purified essentially as follows. An appropriate host cell, such as HEK 293 or CHO, may be either transiently or stably transfected with an expression system for secreting antibodies using an optimal predetermined heavy chain:light chain vector ratio or a single vector system encoding both heavy chain and light chain. Antibody A of the present invention may be either transiently or stably transfected with an expression system for secreting antibodies using one or more DNA molecules encoding for a first heavy chain having the amino acid sequence of SEQ ID NO:5, a first light chain having the amino acid sequence of SEQ ID NO:11, a second heavy chain having the amino acid sequence of SEQ ID NO:17 and a second light chain having the amino acid sequence of SEQ ID NO:23.

The antibodies may be purified using one of many commonly-used techniques. For example, the medium may be conveniently applied to a MabSelect column (GE Healthcare), or KappaSelect column (GE Healthcare), that has been equilibrated with a compatible buffer, such as phosphate buffered saline (pH 7.4). The column may be washed to remove nonspecific binding components. The bound antibody may be eluted, for example, by pH gradient (such as 20 mM Tris buffer pH 7 to 10 mM sodium citrate buffer pH 3.0, or phosphate buffered saline pH 7.4 to 100 mM glycine buffer pH 3.0). Antibody fractions may be detected, such as by UV absorbance or SDS-PAGE, and then may be pooled. Further purification is optional, depending on the intended use. The purified antibody may be concentrated and/or sterile filtered using common techniques. Soluble aggregate and multimers may be effectively removed by common techniques, including size exclusion, hydrophobic interaction, ion exchange, multimodal, or hydroxyapatite chromatography. The purified antibody may be immediately frozen at -70° C. or may be lyophilized.

Antibody A Binds to Human PD-1 and Human CD137

A Biacore® 2000 (GE Healthcare, Piscataway, N.J.) is used to measure the binding kinetics and affinities of Antibody A to soluble human PD-1-extracellular domain (ECD) and human CD137-ECD by surface plasmon resonance at 37° C. Samples are diluted in HBS-EP+ (10 mM HEPES, 150 mM NaCl, 0.05% Tween-20, pH 7.6) running buffer (Teknova Cat #H8022). Protein A (5 mg/mL, Calbiochem Cat #539202) is immobilized on flow cells 1 to 4 of a CM5 senor chip (GE Healthcare Cat #29149604) at a level of 3000 to 4000 response units (RUs) using amine coupling chemistry. Briefly, the surfaces of all four flow cells are activated by injecting a 1:1 mixture of EDC/NHS for 7-minutes at 10 µL/minute. Protein A is diluted to 200 µg/mL in 10 mM acetate, pH 4.5 buffer and immobilized for approximately 3000-4000 RUs onto all four flow cells by 7-minute injection at flow rate of 10 µL/minute. Unreacted sites are blocked with a 7-minute injection of 1M Ethanolamine-HCl pH 8.5 at 10 µL/minute. Five 30-second injections of glycine pH 1.5 at 10 µL/minute are used to remove any non-covalently associated protein.

Binding is evaluated using multi-cycle kinetics by an antibody capture method. Each cycle is performed at 37° C. at a flow rate of 20 or 25 µL/min for antibody capture to the Protein A chip and 100 µL/min for analyte association and dissociation. Each cycle consists of the following steps: injection of antibody at 2.5 µg/mL in HBS-EP+ targeting Rmax values of 50 RU on flow cell, injection of 180 or 200-seconds of analyte in HBS-EP+(concentration range of 1000 nM to 1.95 nM or 5000 nM to 19.5 nM by two-fold serial dilution for PD-1-ECD and CD137-ECD, respectively) followed by 600-second dissociation phase, and regeneration using 5 µL of 10 mM glycine hydrochloride, pH 1.5 over a 30-second contact time utilizing a 10 L/min flow rate. All analyte concentrations are determined utilizing monomeric molecular weight (MW) values. Association rates ($k_{on}$) and dissociation rates ($k_{off}$) for PD-1-ECD are evaluated using double referencing by flow-cell 1 reference subtraction in addition to 0 nM blank subtraction and fit to "1:1 (Langmuir) binding" model in the BIAevaluation software version 4.1. The dissociation constant ($K_D$) is calculated from the binding kinetics according to the relationship $K_D = K_{off}/K_{on}$. Values are reported as mean±standard deviation. CD137-ECD binding data are evaluated using double referencing and fit using a "Steady State Affinity" binding model to determine affinity ($K_D$) utilizing Scrubber2 version 2.0c (BioLogic Software Ltd.).

In experiments performed essentially as described above, Antibody A binds to human PD-1-ECD (Sino Biologicals, Cat #10377-H08H) and human CD137-ECD (in-house generated) with comparable affinity as compared to the respective parental antibodies, as shown in Table 10.

TABLE 10

|  | Human PD-1 $K_D$ (nM) | Human CD137 $K_D$ (nM) |
|---|---|---|
| Antibody A | 2.9 ± 0.1 | 455 ± 66 |
| p-11444 | 3.1 ± 0.1 | Not tested |
| p-7A5 | Not tested | 341 ± 72 |

The Parental Antibody of Antibody A Binds to Human CD137 at Specific Amino Acid Residues that are Distinct from BMS20H4.9

Point mutations are introduced to human CD137 to determine the amino acid residues where p-7A5 (the parental antibody of the anti-CD137 arm of Antibody A) and BMS20H4.9 bind to human CD137. As used herein, BMS20H4.9 refers to an antibody that has been previously described in U.S. Pat. No. 7,288,638. The CD137-Fc mutants are generated using the standard protocol of a commercially-available site directed mutagenesis kit (Quickchange II kit, Qiagen). The wild-type and mutant CD137-Fc proteins are expressed and purified. All the mutants reported here have a size exclusion profile similar to that of the wild-type CD137-Fc (i.e. the mutations introduced do not compromise the structural integrity of the protein). To determine the impact of a mutation on the binding of the antibodies, a point ELISA assay against CD137-Fc wild type and mutants is utilized. The wells of a 96-well Immulon 4HBX ELISA plate are coated overnight with 50 nanograms of human CD137-ECD-C121S-Fc or its mutants in 100 microliters of PBS, pH 7.2 with mild agitation at 4° C. After blocking (with 5% BSA in PBST) and washing, a five-fold dilution eight-point series (100 to 0.00128 nanomolar) of the designated antibody is added and incubated with mild agitation at room temperature for 1 h. The wells are washed and a HRP-conjugated secondary antibody (1:10000 dilution of HRP-conjugated goat anti-Fab antibody (Jackson ImmunoResearch Laboratories) is added and incubated at room temperature following standard protocol. TMB peroxidase chromogenic substrate and stop solution are used according to manufacturer's instruction for visualization and detection of signals. Absorbance readings for each concentration point is normalized by the absorbance of the wild-type interaction. For each mutant, the mean of the normalized ratio for the eight concentrations is determined.

Mutations were individually introduced into human CD137 (SEQ ID NO: 26) at positions: P27, N42, D63, Q67, A97, G98, S100, M101, Q104, K114, K115, R130, I132, and R134. Table 11 shows the binding profiles of BMS20H4.9 and p-7A5 for the shown mutants of human CD137, demonstrating that p-7A5 binds to distinct amino acid residues on human CD137 as compared to BMS20H4.9. In previous studies on IFNγ production in human PBMC co-stimulation assays, p-7A5 enhances the sub-optimal activation of human PBMCs by CD3/CD28 co-stimulation. In this regard, treatment with p-7A5 at 5 micrograms/ml results in a 3.8-fold increase in the production of IFN-gamma that was higher than PF83 (1.6-fold increase) and lower than BMS20H4.9 (9.4-fold increase). As used herein, PF83 refers to an antibody has been previously described in U.S. Pat. No. 8,337,850.

TABLE 11

|  | BMS20H4.9 (% of binding relative to wild-type hCD137) | p-7A5 (% of binding relative to wild-type hCD137) |
|---|---|---|
| P27L* | 85 | 100 |
| N42S* | 0 | 100 |
| D63N | 100 | 100 |
| Q67R | 100 | 100 |
| Q67V | 100 | 100 |
| A97P | 100 | 15 |
| G98K | 100 | 85 |
| G98Q | 100 | 100 |
| S100T | 100 | 100 |
| M101R | 100 | 100 |
| Q104K | 100 | 100 |
| K114E | 100 | 20 |
| K115Q | 100 | 25 |

*Denotes positions that are outside the epitope of Antibody 7A5 as determined via X-Ray Crystallography at 6 Å

Antibody A Antagonizes Human PD-1/PD-L1 Activity

The ability of Antibody A to antagonize the activity mediated by PD-1 ligation to PD-L1 is tested using an NFAT-Luc reporter assay. Briefly, CHO-K1 cells expressing PD-L1 and an artificial cell surface TCR (T cell receptor) activator (Promega proprietary) (Promega CS187108, part of PD1/PD-L1 Blockade Assay System, Propagation Model CS187109) are used as antigen presenting cells. Human CD137 is introduced by retroviral transfer into Jurkat cells expressing PD-1 and an NFAT-Luc2 reporter (GloResponse NFAT-luc2/PD-1 Jurkat, Promega CS187102, part of PD1/PD-L1 Blockade Assay System, Propagation Model CS187109). CHO-K1+PD-L1+ TCR activator cells (at passages 7-9) are detached with trypsin and seeded at 40,000 cells/well in white opaque 96-well tissue culture plates (Costar 35-3296) in 100 ul of growth medium. CHO-K1+ PD-L1+TCR activator growth medium consists of Ham's F-12 medium (Corning Cellgro 10-080-CV) with 10% defined FBS (HyClone SH30070.03), 200 µg/ml hygromycin B (Thermo Fisher 10687-010), and 250 µg/ml G418 (Geneticin, Corning 30-234-CI). Cells are grown overnight at 37° C., 5% $CO_2$, and 95% RH. On the following day, antibodies are prepared with 2× working concentration in RPMI 1640 with 2 mM L-glutamine and 10 mM HEPES (Gibco 22400) with 2% defined FBS (HyClone SH30070.03).

Jurkat cells expressing PD-1, CD137, and an NFAT-Luc2 reporter are propagated in RPMI 1640 with 2 mM L-glutamine and 10 mM HEPES (Gibco), 10% defined FBS (HyClone), 100 µg/ml hygromycin B (Thermo Fisher), 500 µg/ml G418 (Geneticin, Corning), and 1 µg/ml puromycin (Calbiochem 540411, in sterile water). To prepare these Jurkat effector cells (at between passages 5 to 7) for the assay, they are centrifuged, and resuspended in RPMI/2% defined FBS at a concentration of 1.25×$10^6$ cells/ml. 95 µl of media are carefully removed from the monolayers of CHO+ PD-L1+TCR activator cells in the 96-well plates. 40 µl of 2× treatments (including medium alone control) are added per well, with triplicate wells per treatment. Then, 40 µl of Jurkat+PD1+CD137+NFAT-Luc2 cells are added per well (50,000 cells/well). Assay plates are incubated for 6 hours at 37° C., 5% $CO_2$, 95% RH. Plates are equilibrated for 5-10 minutes at room temperature (RT) at the end of incubation. 80 µl per well of reconstituted Bio-Glo™ luciferase substrate (Promega G7940) are added per well and incubated for 5-10 minutes at RT. Plates are read on a Perkin Elmer Envision Multimode Reader, with EnVision Manager software v.1.13.3009.1409, ultrasensitive mode, and a 0.2 second integration time. Within each plate, luminescence values (relative light unit (RLU)) are normalized to values obtained from cells treated with medium alone (Fold Induction=RLU treatment/RLU medium alone control). $EC_{50}$ values are calculated using GraphPad Prism 7 software.

In experiments performed essentially as described above, $EC_{50}$ values for Antibody A and the parental antibody of the anti-PD-1 arm of Antibody A are 7.31 nM and 1.40 nM, respectively.

Antibody A Agonizes Human CD137

Both human PD-1 and CD137 are expressed or co-expressed in activated tumor infiltrating lymphocytes. Thus, the ability of Antibody A to agonize human CD137-mediated activity is tested in Jurkat NFkB-Luc reporter assays, in which Jurkat T cells are engineered to co-express human PD-1 (9,000 PD-1 molecules per cell) and CD137 (5,500 CD137 molecules per cell). Briefly, antibodies are incubated with Jurkat+CD137+PD1+NFkB-Luc cells for 6 hours. Bio-Glo luciferase substrate is added and luminescence is read at the end of incubation. Data (Fold Induction=RLU treatment/RLU medium alone control) are represented as the mean of triplicate wells per treatment.

In experiments performed essentially as described above, Antibody A exhibits greater dose-dependent CD137 agonistic activity than that of p-7A5 and PF-83 when PD-1 is expressed on the same cell as CD137, but lower than that of BMS20H4.9, as shown in Table 2. Data is represented as the mean fold change in luciferase signal from medium alone control (n=3 per treatment).

TABLE 12

| Antibody concentration (nM) | Antibody A | p-7A5 | PF83 | BMS20H4.9 |
| --- | --- | --- | --- | --- |
| 0 | 1.00 | 1.00 | 1.00 | 1.00 |
| 0.01 | 1.02 | 0.98 | 1.00 | 1.00 |
| 0.04 | 1.04 | 0.88 | 0.97 | 1.05 |
| 0.15 | 1.41 | 0.94 | 0.98 | 1.67 |
| 0.59 | 2.35 | 1.07 | 0.95 | 3.54 |
| 2.34 | 3.13 | 1.66 | 1.00 | 4.98 |
| 9.38 | 3.20 | 2.29 | 1.01 | 5.44 |
| 37.50 | 3.04 | 2.72 | 0.99 | 6.21 |
| 150.00 | 2.64 | 2.60 | 1.07 | 5.95 |

Antibody A Enhances IFNγ Generation by Human PBMCs

The functional activity of Antibody A can be examined for its ability to promote IFNγ production using a human PBMC co-stimulation assay. Human PBMCs are isolated from whole blood or leukopac (NY Blood Center, AllCells or BioSpec) using Ficoll density gradient centrifugation (Ficoll-Paque PLUS; GE Healthcare) and grown in RPMI (Life Technologies) with 10% Fetal Calf Serum (HyClone). Anti-human CD3 antibody clone HIT3 (BD Biosciences; 555336) in PBS is coated onto a 96-well plate (typical range: 3 to 5 ng/well). The coated plate is then incubated at 4° C. overnight. After aspirating, the coated wells are rinsed with PBS. Human PBMCs are added onto the coated 96-well plate at a density of $1.5 \times 10^5$ cells/well. Antibody A, Antibody p-11444 (the parental antibody of the anti-PD1 arm of Antibody A), Antibody p-7A5 (the parental antibody of the anti-CD137 arm of Antibody A), and control human IgG1 are prepared by diluting 1:4 down in RPMI-10% FBS at a starting concentration of 80 µg/mL. CD28 antibody (BioLegend; 302933) is added to the plate (typical range 0.4 to 2 µg/mL) followed by the test antibody and incubated for 96 hr at 37° C. in a humidified 5% $CO_2$ incubator. Supernatants are collected and human IFNγ levels are measured using a R&D Systems DuoSet ELISA Kit DY285. Briefly, IFNγ capture antibody is coated onto a plate (100 µg/mL) overnight at room temperature. After aspirating and washing, the plate is blocked for one hour at room temperature. Sample supernatants and IFNγ standard are added and incubated for two hours at room temperature. After washing, 100 µg/mL IFNγ detection antibody is added, incubated for two hours at room temperature followed by washing. Streptavidin-HRP (100 µL of 1:40 dilution) is added for 20 min at room temperature. After washing, 100 µL substrate solution for 20 min is added followed by 50 µL of stop solution, and the signal captured at 450 nm using a SpectraMax microplate reader (Molecular Devices). Data analysis is performed using SoftMax Pro software and GraphPad Prism (GraphPad Software). Fold induction is calculated as sample mean IFNγ (pg/ml)/control human IgG1 mean IFNγ (pg/ml).

In experiments performed essentially as described above, the functional activity of Antibody A with respect to IFNγ production (fold induction) by human PBMCs is comparable to that of the combination of the parental antibodies, as shown in Table 13 below.

TABLE 13

Fold-induction of IFNγ by Antibody A or parental Abs alone or in combination

| Concentration (µg/mL) | p-7A5 | p-11444 | p-7A5 + p-11444 | Antibody A |
| --- | --- | --- | --- | --- |
| 80 | 1.7 | 3.3 | 2.9 | 3 |
| 20 | 2.2 | 4.5 | 3.2 | 4 |
| 5 | 4.6 | 9.3 | 6.1 | 7.3 |
| 1.25 | 4.7 | 9.4 | 8.3 | 10.5 |
| 0.31 | 3.1 | 5.2 | 5.2 | 4.5 |
| 0.078 | 1.7 | 3.0 | 2.7 | 2.3 |

Antibody A Induces a Unique Immune-Gene Expression Pattern in the H292 NSCLC Winn Tumor Model The expression of human immune-related genes (QuantiGene 80-plex) in tumor tissue samples from H292 Winn model treated with Antibody A, Antibody p-7A5, Antibody p-11444, and/or control human IgG1 is examined. Briefly, mice are intraperitoneally injected with a mix of H292 tumor cells and frozen human peripheral blood mononuclear cells on day 0. Antibodies and control human IgG1 are dosed at 10 mg/kg and given on day 1, 8 and 15. Tumor tissues are collected on day 16 and snap-frozen in liquid $N_2$. Snap-frozen tumor tissues are lysed (MagMAX-96 Total RNA isolation kit from Life Technologies) and homogenized (TissueLyser from Qiagen). Total RNA is isolated using MagMAX Express-96 Deep Well Magnetic Particle Processor (Life Technologies) and quantified by spectrophotometer at optical density of 260 and 280 nm. Total RNAs (500 ng) are then analyzed for gene expressions using a QuantiGene 2.0 plex assay (Affymetrix) and analysis is performed using a FLEXMAP 3D Luminex instrument (ThermoFisher). MFI data are converted to relative gene expression (normalized adjusted net MFI) using a quality control analysis script. Fold changes of gene expression for each gene compared to control group is calculated by a formula (normalized adjusted net MFI treatment sample/mean normalized adjusted net MFI). Statistical analysis of mean fold change of each gene compared to control is performed by one-way ANOVA.

In experiments performed essentially as described above, gene expression analysis shows that Antibody A induces a unique immune-related gene expression pattern in H292 tumor tissues in vivo, including genes associated with T cell infiltration and activation (e.g., CD3E, CD4, CD8B, IFNγ, GZMB), multiple cytokines and chemokines, and MHC class I and II antigens (e.g., HLA-B, HLA-DRA). The observed profile in response to Antibody A is distinct from that observed for the parental antibodies of Antibody A and the combinations thereof, as shown in Table 14.

TABLE 14

| Gene | Fold Change | | | | P-value | | | |
|---|---|---|---|---|---|---|---|---|
| | Antibody A | p-7A5 | p-11444 | p-7A5 + p-11444 | Antibody A | p-7A5 | p-11444 | p-7A5 + p-11444 |
| CD3E | 7.26 | 2.11 | 0.81 | 1.76 | 0.00 | 0.20 | 0.72 | 0.36 |
| CD4 | 5.12 | 1.73 | 0.7 | 1.07 | 0.01 | 0.34 | 0.53 | 0.91 |
| CD8B | 9.04 | 3.48 | 1.3 | 3.89 | 0.00 | 0.03 | 0.64 | 0.03 |
| IFNγ | 8.27 | 2.62 | 0.87 | 1.30 | 0.00 | 0.08 | 0.80 | 0.64 |
| HLA-B | 2.23 | 1.38 | 0.73 | 1.08 | 0.02 | 0.27 | 0.29 | 0.79 |
| HLA-DRA | 4.81 | 1.86 | 0.52 | 1.24 | 0.02 | 0.30 | 0.28 | 0.73 |
| CCL5 | 9.56 | 2.39 | 1.06 | 3.30 | 0.00 | 0.16 | 0.92 | 0.07 |
| CXCL10 | 11.05 | 2.95 | 0.54 | 1.58 | 0.01 | 0.20 | 0.46 | 0.60 |
| GZMB | 8.22 | 3.06 | 0.53 | 2.28 | 0.01 | 0.10 | 0.35 | 0.25 |
| PRF1 | 11.59 | 3.45 | 0.65 | 2.48 | 0.00 | 0.08 | 0.52 | 0.22 |

Antibody A Induces T Cell Activation in a Mixed Leukocyte (MLR Reaction)

The PD1 blocking function of Antibody A is examined in human allo MLR assays. Human PBMCs are obtained either frozen (AllCells) or from fresh whole blood subjected to plasmapheresis (Indiana Blood Center) and separated on a Ficoll-Paque PLUS (GE Healthcare) density gradient. CD14$^+$ monocytes are isolated with Human Monocyte Isolation Kit II or CD14 Microbeads (Miltenyi Biotec) and an AutoMACS Pro separator (Miltenyi Biotec). Immature dendritic cells (DCs) are generated by culturing monocytes in complete RPMI-1640 medium containing 10% FBS in the presence of 1,000 IU/mL hGM-CSF (R&D; 215-GM-050, or Sanofi; Leukine, sargramostim; NDC 0024-5843-01) and 500 IU/mL hIL-4 (R&D; 204-IL-050, or another source) for 2 days (Table 14) or 5 days (Tables 16 and 17). CD4$^+$ T cells are purified from fresh human PBMCs of different healthy donors (AllCells or Indiana Blood Center) using a Human CD4$^+$ T Cell Isolation Kit (Miltenyi Biotec). The two types of cells from different donors are then mixed in 96-well V-bottom plates in complete AIM-V medium (Thermo Fisher Scientific) containing $5 \times 10^4$-$1 \times 10^5$ CD4$^+$ T cells and $5 \times 10^3$ immature DCs per well. Human IgG1-EN, p-11444, p-7A5, and Antibody A are tested. Serially diluted control or test antibodies are added to the plates in 8 replicates (100 µL/well) and incubated for 67 hours at 37° C. in 5% CO$_2$ or test antibodies are added to plates in 3 replicates (200 µL/well) and incubated for 4 days. Supernatants are harvested and subjected to human IFN-γ ELISA (R&D Systems; SIF50, or DY285) and human IL-2 ELISA (R&D Systems; S2050) according to manufacturer's instructions. The antibodies are tested across nine different donor pairs. EC50 values are calculated using data from three T:DC donor pairs, with GraphPad Prism software (GraphPad Software).

In the MLR assay using allogeneic human DCs and CD4$^+$ T cells, addition of p-11444, the combination of p-11444 and p-7A5, and Antibody A, each enhances T cell activation in a dose-dependent manner relative to human IgG1. As shown in Table x, mean EC$_{50}$ for IFN-γ and IL-2 production increases. This assay is not able to detect the activity of anti-CD137 Ab.

In conclusion, across several donor pairs, Antibody A retains anti-PD-1 blocking function, similar to p-11444 antibody, alone as measured by increased cytokine release in allogeneic MLR assays.

TABLE 15

PD1 blocking activity of Antibody A in MLR assay (cytokine mean EC50 (nM) values across 3 donors

| Abs | Control IgG1 | p-11444 | p-7A5 | p-11444 + p-7A5 | Antibody A |
|---|---|---|---|---|---|
| IFN-γ | >32 | 0.088 ± 0.071 | >32 | 0.038 ± 0.013 | 0.091 ± 0.074 |
| IL-2 | >32 | 0.238 ± 0.209 | >32 | 0.158 ± 0.063 | 0.297 ± 0.305 |

Antibody A Demonstrates Antitumor Efficacy in a H292 NSCLC Winn Tumor Model

The tumor growth inhibition of H292 tumor xenografts treated with Antibody A, p-11444, p-7A5 and p-11444+p-7A5 is examined. Female NOD/SCID Gamma (NSG) mice (Jackson Laboratories) are used in these studies. Human NSCLC cell line NCI-H292 (ATCC; CRL-1848) and human PBMCs (Stem Cell Technologies) are combined at a 4:1 ratio of tumor cells to PBMC. The mixture is centrifuged and pellet re-suspended in HBSS at a concentration of $10 \times 10^6$ NCI-H292 cells and $2.5 \times 10^6$ PBMC per mL. Each mouse is implanted subcutaneously on the right flank with 0.2 mL of the solution on day 0. One control group receiving tumor cells alone is included in each study. Mice are randomly assigned to treatment groups of 8 mice and treatment started on Day 1. Treatment groups include control IgG, p-7A5, p-11444, the combination of p-11444+p-7A5, and Antibody A. Animals are dosed intraperitoneally (ip) at 10 mg/kg once weekly for 4 weeks. Body weight and tumor volume are measured twice per week. Tumor volume (mm$^3$) is calculated by formula π/6*Length*Width$^2$ and % T/C by formula 100×ΔT/ΔC, if ΔT>0 of the geometric mean values. Statistical analysis is performed using the MIXED procedures in SAS software.

The data ub Table 16 demonstrate that Antibody A treatment at 10 mg/kg inhibits tumor growth (% T/C=~2%, p<0.001) relative to control IgG with 6 of 8 animals achieving complete responses (CR). The combination of p-11444+p-7A5 and monotherapy p-7A5 or p-11444 did not show efficacy.

TABLE 16

| Treatment/Comparison | Xenograft | p-value for tumor volume | T/C % | CR |
|---|---|---|---|---|
| Control IgG 10 mg/kg | NCI-H292 | p = .695 | 115.8 | 0/8 |
| Control IgG 10 mg/kg | NCI-H292 + hPBMC | NA | NA | 0/8 |

TABLE 16-continued

| Treatment/Comparison | Xenograft | p-value for tumor volume | T/C % | CR |
|---|---|---|---|---|
| p-11444 10 mg/kg | NCI-H292 + hPBMC | p = .377 | 71.5 | 1/8 |
| p-7A5 10 mg/kg | NCI-H292 + hPBMC | p = .702 | 115.4 | 1/8 |
| p-11444 + p-7A5 10 mg/kg | NCI-H292 + hPBMC | p = .144 | 57.0 | 1/8 |
| Antibody A 10 mg/kg | NCI-H292 + hPBMC | p < .001 | 1.9 | 6/8 |

NA = not applicable

```
Amino Acid and Nucleotide Sequences
Sequences of 7A5*
<SEQ ID NO: 1; PRT1; ARTIFICIAL SEQUENCE>
KASGGTFSSYAIS

<SEQ ID NO: 2; PRT1; ARTIFICIAL SEQUENCE>
GIIPIFGTANYAQKFQG

<SEQ ID NO: 3; PRT1; ARTIFICIAL SEQUENCE>
ARDLATTAPATYFDL

<SEQ ID NO: 4; PRT1; ARTIFICIAL SEQUENCE>
QVQLVQSGAEVKKPGSSVKVSCKASGGTFSSYAISWVRYAPGQGLEWMGGIIPIF

GTANYAQKFQGRVTITADESTSTAYMELSSLRSEDTAVYYCARDLATTAPATYF

DLWGRGTLVTVSS

<SEQ ID NO: 5; PRT1; ARTIFICIAL SEQUENCE>
QVQLVQSGAEVKKPGSSVKVSCKASGGTFSSYAISWVRYAPGQGLEWMGGIIPIF

GTANYAQKFQGRVTITADESTSTAYMELSSLRSEDTAVYYCARDLATTAPATYF

DLWGRGTLVTVSSASTKGPSVFPLAPCSKSTSGGTAALGCLVKDYFPEPVTVSW

NSGALTSGVHTFPAVLQSSGLYSLSSVVTVPSSSLGTQTYICNVNHKPSNTKVDK

RVEPDSGDKTHTCPPCPAPEAAGGPSVFLFPPKPKDTLMISRTPEVTCVVVDVSHE

DPEVKFNWYVDGVEVHNAKTKPREEQYQSTYRVVSVLTVLHQDWLNGKEYKC

KVSNKALPAPIEKTISKAKGQPREPQVYTLPPSRGDMTKNQVQLTCLVKGFYPSD

IAVEWESNGQPENNYKTTPPVLDSDGSFFLASKLTVDKSRWQQGNVFSCSVMHE

ALHNHYTQKSLSLSPGK

<SEQ ID NO: 6; DNA; ARTIFICIAL SEQUENCE>
CAGGTTCAGTTGGTGCAATCAGGCGCAGAGGTAAAAAAACCAGGGTCCAGCG

TGAAAGTCTCATGTAAGGCCTCCGGCGGAACATTCTCCTCCTACGCTATTTCT

TGGGTGAGATACGCCCCTGGGCAGGGACTTGAGTGGATGGGAGGCATTATTC

CCATATTCGGCACAGCCAATTACGCGCAAAAATTCCAGGGGAGGGTTACTAT

AACAGCAGATGAGAGTACATCAACTGCGTACATGGAACTGAGCTCCCTGAGG

AGCGAAGACACCGCTGTTTACTACTGCGCTAGAGATCTTGCGACGACCGCAC

CTGCGACGTACTTTGATCTCTGGGGTAGAGGAACCCTCGTAACAGTGTCTTCC

GCTAGCACCAAGGGCCCATCGGTCTTCCCCCTGGCACCCTGCTCCAAGAGCAC

CTCTGGGGGCACAGCGGCCCTGGGCTGCCTGGTCAAGGACTACTTCCCCGAA

CCGGTGACGGTGTCGTGGAACTCAGGCGCCCTGACCAGCGGCGTGCACACCT

TCCCGGCTGTCCTACAGTCCTCAGGACTCTACTCCCTCAGCAGCGTGGTGACC

GTGCCCTCCAGCAGCTTGGGCACCCAGACCTACATCTGCAACGTGAATCACA

AGCCCAGCAACACCAAGGTGGACAAGAGAGTTGAGCCCGATTCTGGTGACAA

AACTCACACATGCCCACCGTGCCCAGCACCTGAAGCGCCGGGGGACCGTCA

GTCTTCCTCTTCCCCCCAAAACCCAAGGACACCCTCATGATCTCCCGGACCCC
```

```
-continued
TGAGGTCACATGCGTGGTGGTGGACGTGAGCCACGAAGACCCTGAGGTCAAG

TTCAACTGGTATGTGGACGGCGTGGAGGTGCATAATGCCAAGACAAAGCCGC

GGGAGGAGCAGTACCAGAGCACGTACCGTGTGGTCAGCGTCCTCACCGTCCT

GCACCAAGACTGGCTGAATGGCAAGGAGTACAAGTGCAAGGTCTCCAACAAA

GCCCTCCCAGCCCCCATCGAGAAAACCATCTCCAAAGCCAAAGGGCAGCCCC

GAGAACCACAGGTGTACACCCTGCCCCCATCCCGGGGGACATGACCAAGAA

CCAAGTCCAGCTGACCTGCCTGGTCAAAGGCTTCTATCCCAGCGACATCGCCG

TGGAGTGGGAGAGCAATGGGCAGCCGGAGAACAACTACAAGACCACGCCTC

CCGTGCTGGACTCCGACGGCTCCTTCTTCCTCGCTTCCAAGCTCACCGTGGAC

AAGAGCAGGTGGCAGCAGGGGAACGTCTTCTCATGCTCCGTGATGCATGAGG

CTCTGCACAACCACTACACGCAGAAGAGCCTCTCCCTGTCTCCGGGCAAA

<SEQ ID NO: 7; PRT1; ARTIFICIAL SEQUENCE>
QASQDIGNSLG

<SEQ ID NO: 8; PRT1; ARTIFICIAL SEQUENCE>
FDASDLET

<SEQ ID NO: 9; PRT1; ARTIFICIAL SEQUENCE>
QQGNSFPLT

<SEQ ID NO: 10; PRT1; ARTIFICIAL SEQUENCE>
DIRMTQSPPSLSASVGDRVTITCQASQDIGNSLGWYQRKPGDAPKLVIFDASDLET

GVPSRFSGSGSGTDFSLTISSLQPEDFATYYCQQGNSFPLTFGQGTRLEIK

<SEQ ID NO: 11; PRT1; ARTIFICIAL SEQUENCE>
DIRMTQSPPSLSASVGDRVTITCQASQDIGNSLGWYQRKPGDAPKLVIFDASDLET

GVPSRFSGSGSGTDFSLTISSLQPEDFATYYCQQGNSFPLTFGQGTRLEIKRTVAAP

SVFIFPPSKEQLKSGTASVVCLLNNFYPREAKVQWKVDNALQSGNSQESVTEQDS

KDSTYSLSSTLTLSKADYEKHKVYACEVTHQGLSSPVTKSFNRGEC

<SEQ ID NO: 12; DNA; ARTIFICIAL SEQUENCE>
GACATTAGAATGACACAGTCACCTCCAAGTCTGTCAGCCAGTGTTGGCGACC

GGGTGACTATCACCTGCCAGGCTTCCCAAGACATTGGTAATAGTTTGGGTTGG

TACCAGCGCAAACCAGGCGATGCTCCGAAACTGGTTATTTTTGACGCCAGTG

ATTTGGAGACAGGTGTGCCTTCTCGGTTTAGCGGTTCTGGGTCAGGAACTGAT

TTTTCACTGACAATATCTTCACTGCAGCCGGAAGACTTCGCCACCTATTATTG

CCAGCAGGGGAACTCCTTCCCACTCACCTTCGGTCAAGGGACCCGGCTTGAG

ATTAAGCGGACGGTAGCTGCCCCCTCTGTGTTCATTTTCCCCCCAAGCAAGGA

GCAGCTGAAGAGCGGCACGGCCAGCGTGGTATGTCTGCTGAATAACTTTTAC

CCTCGGGAGGCCAAAGTGCAGTGGAAGGTCGATAATGCTCTTCAATCCGGGA

ACTCACAGGAATCTGTCACCGAACAAGACAGCAAGGATAGCACGTACAGCCT

GTCTAGCACTCTGACCCTTTCCAAAGCAGACTACGAAAAACATAAAGTCTAC

GCGTGCGAAGTGACCCACCAGGGGCTCAGCTCACCGGTGACGAAATCCTTCA

ACCGCGGCGAATGC

Sequences of 11444*
<SEQ ID NO: 13; PRT1; ARTIFICIAL SEQUENCE>
KASGGTFSSYAIS

<SEQ ID NO: 14; PRT1; ARTIFICIAL SEQUENCE>
LIIPSFDTAGYAQEFQG

<SEQ ID NO: 15; PRT1; ARTIFICIAL SEQUENCE>
ARAEHSSTGTFDY
```

<SEQ ID NO: 16; PRT1; ARTIFICIAL SEQUENCE>
QVQLVQSGAEVKKPGSSVKVSCKASGGTFSSYAISWVRKAPGQGLEWMGLIIPSF

DTAGYAQEFQGRVAITVDESTSTAYMELSSLRSEDTAVYYCARAEHSSTGTEDY

WGQGTLVTVSS

<SEQ ID NO: 17; PRT1; ARTIFICIAL SEQUENCE>
QVQLVQSGAEVKKPGSSVKVSCKASGGTFSSYAISWVRKAPGQGLEWMGLIIPSF

DTAGYAQEFQGRVAITVDESTSTAYMELSSLRSEDTAVYYCARAEHSSTGTFDY

WGQGTLVTVSSASTKGPSVFPLAPSSKSTSGGTAALGCLVKDYFPEPVTVSWNSG

ALTSGVATGPAVLQSSGLYSLSSVVTVPSSSLGTQTYICNVNHKPSNTKVDKRVE

PKSCDKTHTCPPCPAPEAAGGPSVFLFPPKPKDTLMISRTPEVTCVVVDVSHEDPE

VKFNWYVDGVEVHNAKTKPREEQYQSTYRVVSVLTVLHQDWLNGKEYKCKVS

NKALPAPIEKTISKAKGQPREPQVSTLPPSREEMTKNQVSLMCLVYGFYPSDIAVE

WESNGQPENNYKTTPPVLDSDGSFFLYSVLTVDKSRWQQGNVFSCSVMHEALH

NHYTQKSLSLSPGK

<SEQ ID NO: 18; DNA; ARTIFICIAL SEQUENCE>
CAAGTGCAACTGGTGCAATCAGGGGCTGAGGTGAAGAAGCCTGGAAGTAGC

GTTAAAGTCAGTTGCAAAGCGTCCGGTGGGACATTTAGCAGCTATGCCATCA

GCTGGGTTCGGAAGGCACCCGGCCAGGGACTGGAGTGGATGGGACTCATAAT

CCCGAGCTTTGACACTGCTGGTTACGCACAGGAGTTTCAAGGGAGGGTGGCG

ATCACAGTGGACGAATCAACCAGCACCGCGTATATGGAGCTGTCATCTCTGA

GGTCAGAAGACACCGCTGTTTACTATTGTGCCCGCGCTGAGCATTCTTCCACC

GGGACCTTCGATTACTGGGGACAAGGAACCCTGGTCACAGTATCATCAGCTA

GCACCAAGGGCCCATCGGTCTTCCCCCTGGCACCCTCCTCCAAGAGCACCTCT

GGGGGCACAGCGGCCCTGGGCTGCCTGGTCAAGGACTACTTCCCCGAACCGG

TGACGGTGTCGTGGAACTCAGGCGCCCTGACCAGCGGCGTGGCCACCGGCCC

GGCTGTCCTACAGTCCTCAGGACTCTACTCCCTCAGCAGCGTGGTGACCGTGC

CCTCCAGCAGCTTGGGCACCCAGACCTACATCTGCAACGTGAATCACAAGCC

CAGCAACACCAAGGTGGACAAGAGAGTTGAGCCCAAATCTTGTGACAAAACT

CACACATGCCCACCGTGCCCAGCACCTGAAGCCGCCGGGGGACCGTCAGTCT

TCCTCTTCCCCCCAAAACCCAAGGACACCCTCATGATCTCCCGGACCCCTGAG

GTCACATGCGTGGTGGTGGACGTGAGCCACGAAGACCCTGAGGTCAAGTTCA

ACTGGTATGTGGACGGCGTGGAGGTGCATAATGCCAAGACAAAGCCGCGGGA

GGAGCAGTACCAGAGCACGTACCGTGTGGTCAGCGTCCTCACCGTCCTGCAC

CAAGACTGGCTGAATGGCAAGGAGTACAAGTGCAAGGTCTCCAACAAAGCCC

TCCCAGCCCCCATCGAGAAAACCATCTCCAAAGCCAAAGGGCAGCCCCGAGA

ACCACAGGTGTCCACCCTGCCCCCATCCCGGGAGGAGATGACCAAGAACCAA

GTCAGCCTGATGTGCCTGGTCATGGCTTCTATCCCAGCGACATCGCCGTGGA

GTGGGAGAGCAATGGGCAGCCGGAGAACAACTACAAGACCACGCCTCCCGT

GCTGGACTCCGACGGCTCCTTCTTCCTCTATTCCGTGCTCACCGTGGACAAGA

-continued

```
GCAGGTGGCAGCAGGGGAACGTCTTCTCATGCTCCGTGATGCATGAGGCTCT

GCACAACCACTACACGCAGAAGAGCCTCTCCCTGTCTCCGGGCAAA
```

<SEQ ID NO: 19; PRT1; ARTIFICIAL SEQUENCE>
RASQGISSWLA

<SEQ ID NO: 20; PRT1; ARTIFICIAL SEQUENCE>
SAASSLQS

<SEQ ID NO: 21; PRT1; ARTIFICIAL SEQUENCE>
QQANHLPFT

<SEQ ID NO: 22; PRT1; ARTIFICIAL SEQUENCE>
```
RIQMTQSPSSVSASVGDRVTITCRASQGISSWLAWYQDKPGKAPKLLISAASSLQS

GVPSRFSGSGSGTDFTLTISSLQPEDFATYYCQQANHLPFTFGGGTKVEIK
```

<SEQ ID NO: 23; PRT1; ARTIFICIAL SEQUENCE>
```
RIQMTQSPSSVSASVGDRVTITCRASQGISSWLAWYQDKPGKAPKLLISAASSLQS

GVPSRFSGSGSGTDFTLTISSLQPEDFATYYCQQANHLPFTFGGGTKVEIKGQPKA

APSVTLFPPSSEELQANKATLVCYISDFYPGAVTVAWKADSSPVKAGVETTTPSK

QSNNKYAAWSYLSLTPEQWKSHRSYSCQVTHEGSTVEKTVAPTEC
```

<SEQ ID NO: 24; DNA; ARTIFICIAL SEQUENCE>
```
CGCATCCAGATGACACAGTCACCTTCAAGCGTCTCCGCCTCCGTGGGAGACA

GGGTTACTATTACATGTAGGGCCAGCCAGGGGATCTCTTCATGGCTGGCGTGG

TACCAAGACAAGCCAGGCAAAGCCCCCAAGCTCCTTATCTCCGCTGCCTCCTC

TCTGCAGTCCGGAGTTCCCTCCCGCTTCAGCGGTAGCGGGTCAGGCACTGACT

TCACCCTTACAATCTCTTCTCTGCAACCTGAGGACTTCGCCACATATTATTGCC

AGCAGGCAAACCATTTGCCATTTACTTTTGGCGGAGGTACTAAGGTTGAGATT

AAAGGCCAGCCTAAAGCTGCCCCTAGCGTTACCCTTTTCCCACCGAGCTCCGA

GGAGCTGCAGGCCAATAAAGCAACCTTGGTCTGCTACATATCAGATTTTTACC

CTGGCGCCGTGACCGTAGCATGGAAAGCTGATTCATCCCCTGTGAAGGCCGG

TGTTGAAACTACAACCCCTTCCAAACAATCTAACAATAAATACGCGGCATGG

TCCTACCTGTCCTTGACACCCGAGCAGTGGAAATCTCACAGATCTTACAGCTG

CCAGGTCACCCACGAGGGGAGCACTGTGGAGAAGACCGTCGCGCCCACTGAG

TGC
```

Sequences of human PD-1 and human CD137
<SEQ ID NO: 25; PRT1; Homo sapiens>
```
MQIPQAPWPVVWAVLQLGWRPGWFLDSPDRPWNPPTFSPALLVVTEGDNATFT

CSFSNTSESFVLNWYRMSPSNQTDKLAAFPEDRSQPGQDCRFRVTQLPNGRDFH

MSVVRARRNDSGTYLCGAISLAPKAQIKESLRAELRVTERRAEVPTAHPSPSPRPA

GQFQTLVVGVVGGLLGSLVLLVWVLAVICSRAARGTIGARRTGQPLKEDPSAVP

VFSVDYGELDFQWREKTPEPPVPCVPEQTEYATIVFPSGMGTSSPARRGSADGPR

SAQPLRPEDGHCSWPL
```

<SEQ ID NO: 26; PRT1; Homo sapiens>
```
MGNSCYNIVATLLLVLNFERTRSLQDPCSNCPAGTFCDNNRNQICSPCPPNSFSSA

GGQRTCDICRQCKGVFRTRKECSSTSNAECDCTPGFHCLGAGCSMCEQDCKQGQ

ELTKKGCKDCCFGTFNDQKRGICRPWTNCSLDGKSVLVNGTKERDVVCGPSPAD

LSPGASSVTPPAPAREPGHSPQIISFFLALTSTALLFLLFFLTLRFSVVKRGRKKLLY

IFKQPFMRPVQTTQEEDGCSCRFPEEEEGGCEL
```

```
Sequence of wild-type human IgG1 constant region
<SEQ ID NO: 27; PRT1; Homo sapiens>
ASTKGPSVFPLAPSSKSTSGGTAALGCLVKDYFPEPVTVSWNSGALTSGVHTFPA

VLQSSGLYSLSSVVTVPSSSLGTQTYICNVNHKPSNTKVDKRVEPKSCDKTHTCPP

CPAPELLGGPSVFLFPPKPKDTLMISRTPEVTCVVVDVSHEDPEVKFNWYVDGVE

VHNAKTKPREEQYNSTYRVVSVLTVLHQDWLNGKEYKCKVSNKALPAPIEKTIS

KAKGQPREPQVYTLPPSREEMTKNQVSLTCLVKGFYPSDIAVEWESNGQPENNY

KTTPPVLDSDGSFFLYSKLTVDKSRWQQGNVFSCSVMHEALHNHYTQKSLSLSP

GK

Sequence of wild-type human Lambda constant region
<SEQ ID NO: 28; PRT1; Homo sapiens>
GQPKAAPSVTLFPPSSEELQANKATLVCLISDFYPGAVTVAWKADSSPVKAGVET

TTPSKQSNNKYAASSYLSLTPEQWKSHRSYSCQVTHEGSTVEKTVAPTEC

Sequence of wild-type human Kappa constant region
<SEQ ID NO: 29; PRT1; Homo sapiens>
RTVAAPSVFIFPPSDEQLKSGTASVVCLLNNFYPREAKVQWKVDNALQSGNSQES

VTEQDSKDSTYSLSSTLTLSKADYEKHKVYACEVTHQGLSSPVTKSFNRGEC

Sequences of the constant regions of Antibody A
7A5*
<SEQ ID NO: 30; PRT1; ARTIFICIAL SEQUENCE>
ASTKGPSVFPLAPCSKSTSGGTAALGCLVKDYFPEPVTVSWNSGALTSGVHTFPA

VLQSSGLYSLSSVVTVPSSSLGTQTYICNVNHKPSNTKVDKRVEPDSGDKTHTCP

PCPAPEAAGGPSVFLFPPKPKDTLMISRTPEVTCVVVDVSHEDPEVKFNWYVDGV

EVHNAKTKPREEQYQSTYRVVSVLTVLHQDWLNGKEYKCKVSNKALPAPIEKTI

SKAKGQPREPQVYTLPPSRGDMTKNQVQLTCLVKGFYPSDIAVEWESNGQPENN

YKTTPPVLDSDGSFFLASKLTVDKSRWQQGNVFSCSVMHEALHNHYTQKSLSLS

PGK

<SEQ ID NO: 31; PRT1; ARTIFICIAL SEQUENCE>
RTVAAPSVFIFPPSKEQLKSGTASVVCLLNNFYPREAKVQWKVDNALQSGNSQES

VTEQDSKDSTYSLSSTLTLSKADYEKHKVYACEVTHQGLSSPVTKSFNRGEC

11444*
<SEQ ID NO: 32; PRT1; ARTIFICIAL SEQUENCE>
ASTKGPSVFPLAPSSKSTSGGTAALGCLVKDYFPEPVTVSWNSGALTSGVATGPA

VLQSSGLYSLSSVVTVPSSSLGTQTYICNVNHKPSNTKVDKRVEPKSCDKTHTCPP

CPAPEAAGGPSVFLFPPKPKDTLMISRTPEVTCVVVDVSHEDPEVKFNWYVDGVE

VHNAKTKPREEQYQSTYRVVSVLTVLHQDWLNGKEYKCKVSNKALPAPIEKTIS

KAKGQPREPQVSTLPPSREEMTKNQVSLMCLVYGFYPSDIAVEWESNGQPENNY

KTTPPVLDSDGSFFLYSVLTVDKSRWQQGNVFSCSVMHEALHNHYTQKSLSLSP

GK

<SEQ ID NO: 33; PRT1; ARTIFICIAL SEQUENCE>
GQPKAAPSVTLFPPSSEELQANKATLVCYISDFYPGAVTVAWKADSSPVKAGVET

TTPSKQSNNKYAAWSYLSLTPEQWKSHRSYSCQVTHEGSTVEKTVAPTEC

Sequences of the variable regions of the parental 7A5
<SEQ ID NO: 34; PRT1; ARTIFICIAL SEQUENCE>
QVQLVQSGAEVKKPGSSVKVSCKASGGTFSSYAISWVRQAPGQGLEWMGGIIPIF

GTANYAQKFQGRVTITADESTSTAYMELSSLRSEDTAVYYCARDLMTTAPGTYF

DLWGRGTLVTVSS
```

<SEQ ID NO: 35; PRT1; ARTIFICIAL SEQUENCE>
AIRMTQSPPSLSASVGDRVTITCQASQDIGNSLGWYQQKPGKAPKLVIFDASDLET

GVPSRFSGSGSGTDFSLTISSLQPEDFATYYCQQGNSFPLTFGQGTRLEIK

Sequences of the variable regions of the parental 11444
<SEQ ID NO: 36; PRT1; ARTIFICIAL SEQUENCE>
QVQLVQSGAEVKKPGSSVKVSCKASGGTFSSYAISWVRQAPGQGLEWMGLIIPM

FDTAGYAQKFQGRVAITVDESTSTAYMELSSLRSEDTAVYYCARAEHSSTGTFD

YWGQGTLVTVSS

<SEQ ID NO: 37; PRT1; ARTIFICIAL SEQUENCE>
DIQMTQSPSSVSASVGDRVTITCRASQGISSWLAWYQQKPGKAPKLLISAASSLQS

GVPSRFSGSGSGTDFTLTISSLQPEDFATYYCQQANHLPFTFGGGTKVEIK

---

We claim:

1. An antibody that antagonizes human PD-1 (SEQ ID NO:25) and agonizes human CD137 (SEQ ID NO:26), comprising a first and second heavy chain and a first and second light chain, wherein each chain comprises a variable region and a constant region, and wherein:
   a) the first heavy chain of the antibody comprises a complementarity-determining region 1 (CDR1) having the amino acid sequence of SEQ ID NO:1, a complementarity-determining region 2 (CDR2) having the amino acid sequence of SEQ ID NO:2, and a complementarity-determining region (CDR3) having the amino acid sequence of SEQ ID NO:3;
   b) the first light chain of the antibody comprises a CDR1 having the amino acid sequence of SEQ ID NO:7, a CDR2 having the amino acid sequence of SEQ ID NO:8, and a CDR3 having the amino acid sequence of SEQ ID NO:9;
   c) the second heavy chain of the antibody comprises a CDR1 having the amino acid sequence of SEQ ID NO:13, a CDR2 having the amino acid sequence of SEQ ID NO:14, and a CDR3 having the amino acid sequence of SEQ ID NO:15; and
   d) the second light chain of the antibody comprises a CDR1 having the amino acid sequence of SEQ ID NO:19, a CDR2 having the amino acid sequence of SEQ ID NO:20, and a CDR3 having the amino acid sequence of SEQ ID NO:21.

2. The antibody of claim 1, wherein:
   a) the variable region of the first heavy chain has the amino acid sequence of SEQ ID NO:4;
   b) the variable region of the first light chain has the amino acid sequence of SEQ ID NO:10;
   c) the variable region of the second heavy chain has the amino acid sequence of SEQ ID NO:16; and
   d) the variable region of the second light chain has the amino acid sequence of SEQ ID NO:22.

3. The antibody of claim 1, wherein:
   a) the first heavy chain of the antibody has the amino acid sequence of SEQ ID NO:5;
   b) the first light chain of the antibody has the amino acid sequence of SEQ ID NO:11;
   c) the second heavy chain of the antibody has the amino acid sequence of SEQ ID NO:17; and
   d) the second light chain of the antibody has the amino acid sequence of SEQ ID NO:23.

4. The antibody of claim 1, wherein the first heavy chain of the antibody forms at least one disulfide bond with the first light chain of the antibody, the second heavy chain of the antibody forms at least one disulfide bond with the second light chain of the antibody, and the first heavy chain of the antibody forms at least one disulfide bond with the second heavy chain of the antibody.

5. The antibody of claim 1, wherein the antibody is a modified human IgG1.

6. A process for producing an antibody comprising cultivating a mammalian cell capable of expressing the antibody and recovering the antibody; wherein the antibody comprises a first and second heavy chain and a first and second light chain, wherein each chain comprises a variable region and a constant region, and wherein:
   a) the first heavy chain of the antibody comprises a CDR1 having the amino acid sequence of SEQ ID NO:1, a CDR2 having the amino acid sequence of SEQ ID NO:2, and a CDR3 having the amino acid sequence of SEQ ID NO:3;
   b) the first light chain of the antibody comprises a CDR1 having the amino acid sequence of SEQ ID NO:7, a CDR2 having the amino acid sequence of SEQ ID NO:8, and a CDR3 having the amino acid sequence of SEQ ID NO:9;
   c) the second heavy chain of the antibody comprises a CDR1 having the amino acid sequence of SEQ ID NO:13, a CDR2 having the amino acid sequence of SEQ ID NO:14, and a CDR3 having the amino acid sequence of SEQ ID NO:15; and
   d) the second light chain of the antibody comprises a CDR1 having the amino acid sequence of SEQ ID NO:19, a CDR2 having the amino acid sequence of SEQ ID NO:20, and a CDR3 having the amino acid sequence of SEQ ID NO:21; optionally, wherein the first heavy chain of the antibody forms at least one disulfide bond with the first light chain of the antibody, the second heavy chain of the antibody forms at least one disulfide bond with the second light chain of the antibody, and the first heavy chain of the antibody forms at least one disulfide bond with the second heavy chain of the antibody.

7. The process of claim 6, wherein:
a) the variable region of the first heavy chain has the amino acid sequence of SEQ ID NO:4;
b) the variable region of the first light chain has the amino acid sequence of SEQ ID NO:10;
c) the variable region of the second heavy chain has the amino acid sequence of SEQ ID NO:16; and
d) the variable region of the second light chain has the amino acid sequence of SEQ ID NO:22.

8. The process of claim 6, wherein:
a) the first heavy chain of the antibody has the amino acid sequence of SEQ ID NO:5;
b) the first light chain of the antibody has the amino acid sequence of SEQ ID NO:11;
c) the second heavy chain of the antibody has the amino acid sequence of SEQ ID NO:17; and
d) the second light chain of the antibody has the amino acid sequence of SEQ ID NO:23.

9. The process of claim 6, wherein the antibody is a human IgG1 engineered to reduce the binding of the antibody to an Fc gamma receptor.

10. A pharmaceutical composition comprising an antibody, wherein the antibody antagonizes human PD-1 (SEQ ID NO:25) and agonizes human CD137 (SEQ ID NO:26), and the antibody comprises a first and second heavy chain and a first and second light chain, wherein each chain comprises a variable region and a constant region, and wherein:
a) the first heavy chain of the antibody comprises a CDR1 having the amino acid sequence of SEQ ID NO:1, a CDR2 having the amino acid sequence of SEQ ID NO:2, and a CDR3 having the amino acid sequence of SEQ ID NO:3;
b) the first light chain of the antibody comprises a CDR1 having the amino acid sequence of SEQ ID NO:7, a CDR2 having the amino acid sequence of SEQ ID NO:8, and a CDR3 having the amino acid sequence of SEQ ID NO:9;
c) the second heavy chain of the antibody comprises a CDR1 having the amino acid sequence of SEQ ID NO:13, a CDR2 having the amino acid sequence of SEQ ID NO:14, and a CDR3 having the amino acid sequence of SEQ ID NO:15; and
d) the second light chain of the antibody comprises a CDR1 having the amino acid sequence of SEQ ID NO:19, a CDR2 having the amino acid sequence of SEQ ID NO:20, and a CDR3 having the amino acid sequence of SEQ ID NO:21; and wherein: the first heavy chain of the antibody forms at least one disulfide bond with the first light chain of the antibody, the second heavy chain of the antibody forms at least one disulfide bond with the second light chain of the antibody, and the first heavy chain of the antibody forms at least one disulfide bond with the second heavy chain of the antibody.

11. The pharmaceutical composition of claim 10, wherein:
a) the variable region of the first heavy chain has the amino acid sequence of SEQ ID NO:4;
b) the variable region of the first light chain has the amino acid sequence of SEQ ID NO:10;
c the variable region of the second heavy chain has the amino acid sequence of SEQ ID NO:16; and
d) the variable region of the second light chain has the amino acid sequence of SEQ ID NO:22.

12. The pharmaceutical composition of claim 10, wherein:
a) the first heavy chain of the antibody has the amino acid sequence of SEQ ID NO:5;
b) the first light chain of the antibody has the amino acid sequence of SEQ ID NO:11;
c) the second heavy chain of the antibody has the amino acid sequence of SEQ ID NO:17; and
d) the second light chain of the antibody has the amino acid sequence of SEQ ID NO:23.

13. The pharmaceutical composition of claim 10, wherein the antibody is a human IgG1 engineered to reduce the binding of the antibody to an Fc gamma receptor.

14. A method of treating cancer comprising administering to a human patient in need thereof, an effective amount of an antibody, wherein the antibody antagonizes human PD-1 (SEQ ID NO:25) and agonizes human CD137 (SEQ ID NO:26), and the antibody comprises a first and second heavy chain and a first and second light chain, wherein each chain comprises a variable region and a constant region, and wherein:
a) the first heavy chain of the antibody comprises a CDR1 having the amino acid sequence of SEQ ID NO:1, a CDR2 having the amino acid sequence of SEQ ID NO:2, and a CDR3 having the amino acid sequence of SEQ ID NO:3;
b) the first light chain of the antibody comprises a CDR1 having the amino acid sequence of SEQ ID NO:7, a CDR2 having the amino acid sequence of SEQ ID NO:8, and a CDR3 having the amino acid sequence of SEQ ID NO:9;
c) the second heavy chain of the antibody comprises a CDR1 having the amino acid sequence of SEQ ID NO:13, a CDR2 having the amino acid sequence of SEQ ID NO:14, and a CDR3 having the amino acid sequence of SEQ ID NO:15; and
d) the second light chain of the antibody comprises a CDR1 having the amino acid sequence of SEQ ID NO:19, a CDR2 having the amino acid sequence of SEQ ID NO:20, and a CDR3 having the amino acid sequence of SEQ ID NO:21; and wherein the first heavy chain of the antibody forms at least one disulfide bond with the first light chain of the antibody, the second heavy chain of the antibody forms at least one disulfide bond with the second light chain of the antibody, and the first heavy chain of the antibody forms at least one disulfide bond with the second heavy chain of the antibody.

15. The method of claim 14, wherein:
a) the variable region of the first heavy chain has the amino acid sequence of SEQ ID NO:4;
b) the variable region of the first light chain has the amino acid sequence of SEQ ID NO:10;
c) the variable region of the second heavy chain has the amino acid sequence of SEQ ID NO:16; and
d) the variable region of the second light chain has the amino acid sequence of SEQ ID NO:22.

16. The method of claim 14, wherein:
a) the first heavy chain of the antibody has the amino acid sequence of SEQ ID NO:5;

b) the first light chain of the antibody has the amino acid sequence of SEQ ID NO:11;
c) the second heavy chain of the antibody has the amino acid sequence of SEQ ID NO:17; and
d) the second light chain of the antibody has the amino acid sequence of SEQ ID NO:23.

17. The method of claim 14, wherein the antibody is a human IgG1 engineered to reduce the binding of the antibody to an Fc gamma receptor.

18. The method of claim 1, wherein the cancer is melanoma, non-small cell lung cancer, small cell lung cancer, head and neck cancer, liver cancer, colorectal cancer, pancreatic cancer, gastric cancer, kidney cancer, bladder cancer, prostate cancer, breast cancer, ovarian cancer, endometrial cancer, esophageal cancer, soft tissue sarcoma, cholangiocarcinoma, thyroid cancer, hepatocellular carcinoma, or mesothelioma.

19. The method of claim 14, wherein the antibody is administered in combination with ionizing radiation.

20. The method of claim 14, wherein the antibody is administered in combination with one or more chemotherapeutic agents.

* * * * *